US010948493B2

(12) United States Patent
Couto et al.

(10) Patent No.: US 10,948,493 B2
(45) Date of Patent: Mar. 16, 2021

(54) ANTIBODIES, COMPOSITIONS, AND IMMUNOHISTOCHEMISTRY METHODS FOR DETECTING C4.4A

(71) Applicant: Ventana Medical Systems, Inc., Tucson, AZ (US)

(72) Inventors: Fernando Jose Rebelo do Couto, Pleasanton, CA (US); Zhiming Liao, Livermore, CA (US); Yifei Zhu, San Jose, CA (US)

(73) Assignee: Ventana Medical Systems, Inc., Tucson, AZ (US)

( * ) Notice: Subject to any disclaimer, the term of this patent is extended or adjusted under 35 U.S.C. 154(b) by 363 days.

(21) Appl. No.: 15/782,804

(22) Filed: Oct. 12, 2017

(65) Prior Publication Data
US 2018/0031566 A1 Feb. 1, 2018

Related U.S. Application Data

(63) Continuation of application No. PCT/EP2016/058135, filed on Apr. 13, 2016.

(60) Provisional application No. 62/149,239, filed on Apr. 17, 2015.

(51) Int. Cl.
*G01N 33/574* (2006.01)
*C07K 16/28* (2006.01)
*C07K 16/30* (2006.01)
*G01N 1/30* (2006.01)

(52) U.S. Cl.
CPC ....... *G01N 33/57492* (2013.01); *C07K 16/28* (2013.01); *C07K 16/30* (2013.01); *C07K 2317/565* (2013.01); *C07K 2317/567* (2013.01); *G01N 1/30* (2013.01)

(58) Field of Classification Search
CPC .... G01N 33/57492; G01N 1/30; C07K 16/30; C07K 16/28; C07K 2317/565; C07K 2317/567
See application file for complete search history.

(56) References Cited

U.S. PATENT DOCUMENTS

| | | | |
|---|---|---|---|
| 2012/0321619 A1 | 12/2012 | Linden et al. | |
| 2012/0322073 A1* | 12/2012 | Lopez-Girona | C07K 16/18 435/6.12 |
| 2013/0095123 A1* | 4/2013 | Lerchen | A61K 31/537 424/179.1 |
| 2015/0147278 A1 | 5/2015 | Masuko et al. | |
| 2017/0283509 A1* | 10/2017 | Logsdson | C12N 15/1138 |

FOREIGN PATENT DOCUMENTS

| | | |
|---|---|---|
| WO | WO03080672 A1 | 10/2003 |
| WO | 2011070088 A1 | 6/2011 |
| WO | WO2011158883 A1 | 12/2011 |
| WO | WO2013183786 A1 | 12/2013 |

OTHER PUBLICATIONS

Anti-C4.4A / LYPD3 Antibody (aa262-311) LS-C186776, LifeSpan BioSciences, Inc., https://www.lsbio.com/antibodies/anti-c4.4a-antibody-lypd3-antibody-aa262-311-wb-western-ls-c186776/194679 (2 pages), downloaded Jan. 11, 2018.
Anti-C4.4A / LYPD3 Antibody (C-Terminus) IHC-plus LS-A9856, LifeSpan BioSciences, Inc., https://www.lsbio.com/antibodies/anti-c4.4a-antibody-lypd3-antibody-c-terminus-ihc-ihc-plus-ls-a9856/63938 (2 pages), downloaded Jan. 11, 2018.
Anti-C4_4A / LYPD3 Antibody (C-Terminus) IHC-plus LS-A9857, LifeSpan BioSciences, Inc., https://www.lsbio.com/antibodies/anti-c4.4a-antibody-c-terminus-ihc-ihc-plus-ls-a9857/63939 (2 pages), downloaded Jan. 10, 2018.
C4.4A / LYPD3 Antibody, Novus Biologicals, https://www.novusbio.com/products/c44a-lypd3-antibody_nbp2-32598 (3 pages), downloaded Jan. 12, 2018.
Human C4.4A Antibody, http://www.Clontech.com, http://www.clontech.com/LY/Products/Cell_Biology_and_Epigenetics/Cancer_and_Inflammation/C4_4A (2 pages), downloaded Jan. 11, 2018.
Rudikoff, Stuart et al, Single amino acid substitution altering antigen-binding specificity, Proceedings of the National Academy of Sciences USA, 1982, pp. 1979-1983, vol. 79, No. 6.
Schneider, C., et al., Abstract 2836: Development of a companion diagnostic Ihc assay for the biomarker-driven selection of C4.4a positive patients, Clinical Research, Oct. 2014, vol. 74, Issue 19 Supplement.
Tamura, Midori et al., Structural Correlates of an Anticarcinoma Antibody: Identification of Specificity-Determining Residues (SDRs) and Development of a Minimally Immunogenic Antibody Variant by Retention of SDRs Only, the Journal of Immunology, 2000, pp. 1432-1441, vol. 164, No. 3.
Anti-C4.4A / LYPD3 Antibody (aa262-311) LS-C186776, LifeSpan BioSciences, Inc., https://www.lsbio.com/antibodies/anti-c4.4a-antibody-lypd3-antibody-aa262-311-wb-western-ls-c186776/194679 (2 pages), Jan. 11, 2018.
Anti-C4.4A / LYPD3 Antibody (C-Terminus) IHC-plus LS-A9856, LifeSpan BioSciences, Inc., https://www.lsbio.com/antibodies/anti-c4.4a-antibody-lypd3-antibody-c-terminus-ihc-ihc-plus-ls-a9856/63938 (2 pages), Jan. 11, 2018.
Anti-C4.4A / LYPD3 Antibody (C-Terminus) IHC-plus LS-A9857, LifeSpan BioSciences, Inc., https://www.lsbio.com/antibodies/anti-c4.4a-antibody-c-terminus-ihc-ihc-plus-ls-a9857/63939 (2 pages), Jan. 10, 2018.

(Continued)

Primary Examiner — Alana Harris Dent
(74) Attorney, Agent, or Firm — Ventana Medical Systems, Inc.

(57) ABSTRACT

Antibodies, compositions, systems, and methods for detecting C4.4a, for example immunohistochemistry methods for detecting C4.4a using a C4.4a antibody. The antibody may be obtained by immunizing a host with a C4.4a protein such as a peptide downstream of the signal peptide. The antibodies may be adapted to detect the uPAR-like domain 1 and uPAR-like domain 2. Also featured are methods for diagnosing C4.4a-associated tumors using C4.4a antibodies disclosed herein.

20 Claims, 4 Drawing Sheets
(4 of 4 Drawing Sheet(s) Filed in Color)

Specification includes a Sequence Listing.

(56) References Cited

OTHER PUBLICATIONS

C4.4A / LYPD3 Antibody, Novus Biologicals, https://www.novusbio.com/products/c44a-lypd3-antibody_nbp2-32598 (3 pages), Jan. 12, 2018.

Hansen et al, Production, characterization and use of mono- and polyclonal antibodies against C4.4A, a homologue of the urokinase receptor, Thrombosis and Haemostasis, Apr. 2005, A33, vol. 93, No. 4, Section 125.

Hansen, L.V. et al., Structural analysis and tissue localization of human C4.4A: a protein homologue of the urokinase receptor, Biochemical Journal, 2004, pp. 845-857, vol. 380.

Human C4.4A Antibody, http://www.Clontech.com, http://www.clontech.com/LY/Products/Cell_Biology_and_Epigenetics/Cancer_and_inflammation/C4_4A (2 pages), Jan. 11, 2018.

International Preliminary Report on Patentability for corresponding PCT/EP2016/058135 filed Apr. 13, 2016, pp. 1-14.

IInternational Search Report and Written Opinion dated Sep. 1, 2016 for corresponding PCT/EP2016/058135 filed Apr. 13, 2016, pp. 1-22.

Wurfel et al, Cloning of the human homologue of the metastasis-associated rat C4.4A, Gene, 2001, pp. 35-41, vol. 262, Elsevier.

* cited by examiner

| | SCC-T9 xenograft (+++ Ctr) | H293-T3 (++ Ctr) |
|---|---|---|
| S42H9L5 |  |  |
| | MCF-7 xenograft (+ Ctr) | PC3(- Ctr) |
| S42H9L5 |  |  |

| | SCC-T9 xenograft (+++ Ctr) | H293-T3 (++ Ctr) |
|---|---|---|
| S20H1L1 |  |  |
| | MCF-7 xenograft (+ Ctr) | PC3(- Ctr) |
| S20H1L1 |  |  |

| | Skin | Skin Squamous Cell Carcinoma |
|---|---|---|
| S42H9L5 |  |  |
| | Cervix | Esophagus |
| S42H9L5 |  |  |

| | Skin | Skin Squamous Cell Carcinoma |
|---|---|---|
| S20H1L1 |  |  |
| | Cervix | Esophagus |
| S20H1L1 |  |  |

SEQUENCE LISTING

```
<160> NUMBER OF SEQ ID NOS: 64

<210> SEQ ID NO 1
<211> LENGTH: 346
<212> TYPE: PRT
<213> ORGANISM: Homo sapiens

<400> SEQUENCE: 1

Met Asp Pro Ala Arg Lys Ala Gly Ala Gln Ala Met Ile Trp Thr Ala
1               5                   10                  15

Gly Trp Leu Leu Leu Leu Leu Leu Arg Gly Gly Ala Gln Ala Leu Glu
            20                  25                  30

Cys Tyr Ser Cys Val Gln Lys Ala Asp Asp Gly Cys Ser Pro Asn Lys
        35                  40                  45

Met Lys Thr Val Lys Cys Ala Pro Gly Val Asp Val Cys Thr Glu Ala
```

```
                    50                  55                  60
Val Gly Ala Val Glu Thr Ile His Gly Gln Phe Ser Leu Ala Val Arg
 65                  70                  75                  80

Gly Cys Gly Ser Gly Leu Pro Gly Lys Asn Asp Arg Gly Leu Asp Leu
                 85                  90                  95

His Gly Leu Leu Ala Phe Ile Gln Leu Gln Gln Cys Ala Gln Asp Arg
                100                 105                 110

Cys Asn Ala Lys Leu Asn Leu Thr Ser Arg Ala Leu Asp Pro Ala Gly
            115                 120                 125

Asn Glu Ser Ala Tyr Pro Pro Asn Gly Val Glu Cys Tyr Ser Cys Val
        130                 135                 140

Gly Leu Ser Arg Glu Ala Cys Gln Gly Thr Ser Pro Pro Val Val Ser
145                 150                 155                 160

Cys Tyr Asn Ala Ser Asp His Val Tyr Lys Gly Cys Phe Asp Gly Asn
                165                 170                 175

Val Thr Leu Thr Ala Ala Asn Val Thr Val Ser Leu Pro Val Arg Gly
                180                 185                 190

Cys Val Gln Asp Glu Phe Cys Thr Arg Asp Gly Val Thr Gly Pro Gly
            195                 200                 205

Phe Thr Leu Ser Gly Ser Cys Cys Gln Gly Ser Arg Cys Asn Ser Asp
210                 215                 220

Leu Arg Asn Lys Thr Tyr Phe Ser Pro Arg Ile Pro Pro Leu Val Arg
225                 230                 235                 240

Leu Pro Pro Pro Glu Pro Thr Thr Val Ala Ser Thr Thr Ser Val Thr
                245                 250                 255

Thr Ser Thr Ser Ala Pro Val Arg Pro Thr Ser Thr Thr Lys Pro Met
                260                 265                 270

Pro Ala Pro Thr Ser Gln Thr Pro Arg Gln Gly Val Glu His Glu Ala
            275                 280                 285

Ser Arg Asp Glu Glu Pro Arg Leu Thr Gly Gly Ala Ala Gly His Gln
        290                 295                 300

Asp Arg Ser Asn Ser Gly Gln Tyr Pro Ala Lys Gly Gly Pro Gln Gln
305                 310                 315                 320

Pro His Asn Lys Gly Cys Val Ala Pro Thr Ala Gly Leu Ala Ala Leu
                325                 330                 335

Leu Leu Ala Val Ala Ala Gly Val Leu Leu
                340                 345

<210> SEQ ID NO 2
<211> LENGTH: 278
<212> TYPE: PRT
<213> ORGANISM: Homo sapiens

<400> SEQUENCE: 2

Leu Glu Cys Tyr Ser Cys Val Gln Lys Ala Asp Asp Gly Cys Ser Pro
 1               5                  10                  15

Asn Lys Met Lys Thr Val Lys Cys Ala Pro Gly Val Asp Val Cys Thr
                20                  25                  30

Glu Ala Val Gly Ala Val Glu Thr Ile His Gly Gln Phe Ser Leu Ala
            35                  40                  45

Val Arg Gly Cys Gly Ser Gly Leu Pro Gly Lys Asn Asp Arg Gly Leu
        50                  55                  60

Asp Leu His Gly Leu Leu Ala Phe Ile Gln Leu Gln Gln Cys Ala Gln
 65                  70                  75                  80
```

```
Asp Arg Cys Asn Ala Lys Leu Asn Leu Thr Ser Arg Ala Leu Asp Pro
                85                  90                  95

Ala Gly Asn Glu Ser Ala Tyr Pro Pro Asn Gly Val Glu Cys Tyr Ser
            100                 105                 110

Cys Val Gly Leu Ser Arg Glu Ala Cys Gln Gly Thr Ser Pro Pro Val
            115                 120                 125

Val Ser Cys Tyr Asn Ala Ser Asp His Val Tyr Lys Gly Cys Phe Asp
130                 135                 140

Gly Asn Val Thr Leu Thr Ala Ala Asn Val Thr Val Ser Leu Pro Val
145                 150                 155                 160

Arg Gly Cys Val Gln Asp Glu Phe Cys Thr Arg Asp Gly Val Thr Gly
                165                 170                 175

Pro Gly Phe Thr Leu Ser Gly Ser Cys Cys Gln Gly Ser Arg Cys Asn
            180                 185                 190

Ser Asp Leu Arg Asn Lys Thr Tyr Phe Ser Pro Arg Ile Pro Pro Leu
            195                 200                 205

Val Arg Leu Pro Pro Glu Pro Thr Thr Val Ala Ser Thr Thr Ser
210                 215                 220

Val Thr Thr Ser Thr Ser Ala Pro Val Arg Pro Thr Ser Thr Thr Lys
225                 230                 235                 240

Pro Met Pro Ala Pro Thr Ser Gln Thr Pro Arg Gln Gly Val Glu His
                245                 250                 255

Glu Ala Ser Arg Asp Glu Pro Arg Leu Thr Gly Gly Ala Ala Gly
            260                 265                 270

His Gln Asp Arg Ser Asn
        275

<210> SEQ ID NO 3
<211> LENGTH: 86
<212> TYPE: PRT
<213> ORGANISM: Homo sapiens

<400> SEQUENCE: 3

Leu Glu Cys Tyr Ser Cys Val Gln Lys Ala Asp Asp Gly Cys Ser Pro
1               5                   10                  15

Asn Lys Met Lys Thr Val Lys Cys Ala Pro Gly Val Asp Val Cys Thr
            20                  25                  30

Glu Ala Val Gly Ala Val Glu Thr Ile His Gly Gln Phe Ser Leu Ala
            35                  40                  45

Val Arg Gly Cys Gly Ser Gly Leu Pro Gly Lys Asn Asp Arg Gly Leu
        50                  55                  60

Asp Leu His Gly Leu Leu Ala Phe Ile Gln Leu Gln Gln Cys Ala Gln
65                  70                  75                  80

Asp Arg Cys Asn Ala Lys
                85

<210> SEQ ID NO 4
<211> LENGTH: 86
<212> TYPE: PRT
<213> ORGANISM: Homo sapiens

<400> SEQUENCE: 4

Glu Cys Tyr Ser Cys Val Gly Leu Ser Arg Glu Ala Cys Gln Gly Thr
1               5                   10                  15

Ser Pro Pro Val Val Ser Cys Tyr Asn Ala Ser Asp His Val Tyr Lys
            20                  25                  30
```

Gly Cys Phe Asp Gly Asn Val Thr Leu Thr Ala Ala Asn Val Thr Val
                35                  40                  45

Ser Leu Pro Val Arg Gly Cys Val Gln Asp Glu Phe Cys Thr Arg Asp
 50                  55                  60

Gly Val Thr Gly Pro Gly Phe Thr Leu Ser Gly Ser Cys Cys Gln Gly
 65                  70                  75                  80

Ser Arg Cys Asn Ser Asp
                 85

<210> SEQ ID NO 5
<211> LENGTH: 260
<212> TYPE: PRT
<213> ORGANISM: Homo sapiens

<400> SEQUENCE: 5

Leu Glu Cys Tyr Ser Cys Val Gln Lys Ala Asp Asp Gly Cys Ser Pro
 1               5                  10                  15

Asn Lys Met Lys Thr Val Lys Cys Ala Pro Gly Val Asp Val Cys Thr
                20                  25                  30

Glu Ala Val Gly Ala Val Glu Thr Ile His Gly Gln Phe Ser Leu Ala
                35                  40                  45

Val Arg Gly Cys Gly Ser Gly Leu Pro Gly Lys Asn Asp Arg Gly Leu
 50                  55                  60

Asp Leu His Gly Leu Leu Ala Phe Ile Gln Leu Gln Gln Cys Ala Gln
 65                  70                  75                  80

Asp Arg Cys Asn Ala Lys Leu Asn Leu Thr Ser Arg Ala Leu Asp Pro
                85                  90                  95

Ala Gly Asn Glu Ser Ala Tyr Pro Pro Asn Gly Val Glu Cys Tyr Ser
                100                 105                 110

Cys Val Gly Leu Ser Arg Glu Ala Cys Gln Gly Thr Ser Pro Pro Val
                115                 120                 125

Val Ser Cys Tyr Asn Ala Ser Asp His Val Tyr Lys Gly Cys Phe Asp
                130                 135                 140

Gly Asn Val Thr Leu Thr Ala Ala Asn Val Thr Val Ser Leu Pro Val
145                 150                 155                 160

Arg Gly Cys Val Gln Asp Glu Phe Cys Thr Arg Asp Gly Val Thr Gly
                165                 170                 175

Pro Gly Phe Thr Leu Ser Gly Ser Cys Cys Gln Gly Ser Arg Cys Asn
                180                 185                 190

Ser Asp Leu Arg Asn Lys Thr Tyr Phe Ser Pro Arg Ile Pro Pro Leu
                195                 200                 205

Val Arg Leu Pro Pro Pro Glu Pro Thr Thr Val Ala Ser Thr Thr Ser
                210                 215                 220

Val Thr Thr Ser Thr Ser Ala Pro Val Arg Pro Thr Thr Ser Thr Lys
225                 230                 235                 240

Pro Met Pro Ala Pro Thr Ser Gln Thr Pro Arg Gln Gly Val Glu His
                245                 250                 255

Glu Ala Ser Arg
            260

<210> SEQ ID NO 6
<211> LENGTH: 250
<212> TYPE: PRT
<213> ORGANISM: Homo sapiens

<400> SEQUENCE: 6

Cys Val Gln Lys Ala Asp Asp Gly Cys Ser Pro Asn Lys Met Lys Thr
1               5                   10                  15

Val Lys Cys Ala Pro Gly Val Asp Val Cys Thr Glu Ala Val Gly Ala
            20                  25                  30

Val Glu Thr Ile His Gly Gln Phe Ser Leu Ala Val Arg Gly Cys Gly
        35                  40                  45

Ser Gly Leu Pro Gly Lys Asn Asp Arg Gly Leu Asp Leu His Gly Leu
50                  55                  60

Leu Ala Phe Ile Gln Leu Gln Gln Cys Ala Gln Asp Arg Cys Asn Ala
65                  70                  75                  80

Lys Leu Asn Leu Thr Ser Arg Ala Leu Asp Pro Ala Gly Asn Glu Ser
                85                  90                  95

Ala Tyr Pro Pro Asn Gly Val Glu Cys Tyr Ser Cys Val Gly Leu Ser
            100                 105                 110

Arg Glu Ala Cys Gln Gly Thr Ser Pro Val Val Ser Cys Tyr Asn
        115                 120                 125

Ala Ser Asp His Val Tyr Lys Gly Cys Phe Asp Gly Asn Val Thr Leu
130                 135                 140

Thr Ala Ala Asn Val Thr Val Ser Leu Pro Val Arg Gly Cys Val Gln
145                 150                 155                 160

Asp Glu Phe Cys Thr Arg Asp Gly Val Thr Gly Pro Gly Phe Thr Leu
                165                 170                 175

Ser Gly Ser Cys Cys Gln Gly Ser Arg Cys Asn Ser Asp Leu Arg Asn
            180                 185                 190

Lys Thr Tyr Phe Ser Pro Arg Ile Pro Pro Leu Val Arg Leu Pro Pro
        195                 200                 205

Pro Glu Pro Thr Thr Val Ala Ser Thr Thr Ser Val Thr Thr Ser Thr
210                 215                 220

Ser Ala Pro Val Arg Pro Thr Ser Thr Thr Lys Pro Met Pro Ala Pro
225                 230                 235                 240

Thr Ser Gln Thr Pro Arg Gln Gly Val Glu
            245                 250

<210> SEQ ID NO 7
<211> LENGTH: 245
<212> TYPE: PRT
<213> ORGANISM: Homo sapiens

<400> SEQUENCE: 7

Leu Glu Cys Tyr Ser Cys Val Gln Lys Ala Asp Asp Gly Cys Ser Pro
1               5                   10                  15

Asn Lys Met Lys Thr Val Lys Cys Ala Pro Gly Val Asp Val Cys Thr
            20                  25                  30

Glu Ala Val Gly Ala Val Glu Thr Ile His Gly Gln Phe Ser Leu Ala
        35                  40                  45

Val Arg Gly Cys Gly Ser Gly Leu Pro Gly Lys Asn Asp Arg Gly Leu
50                  55                  60

Asp Leu His Gly Leu Leu Ala Phe Ile Gln Leu Gln Gln Cys Ala Gln
65                  70                  75                  80

Asp Arg Cys Asn Ala Lys Leu Asn Leu Thr Ser Arg Ala Leu Asp Pro
                85                  90                  95

Ala Gly Asn Glu Ser Ala Tyr Pro Pro Asn Gly Val Glu Cys Tyr Ser
            100                 105                 110

Cys Val Gly Leu Ser Arg Glu Ala Cys Gln Gly Thr Ser Pro Pro Val
        115                 120                 125

```
Val Ser Cys Tyr Asn Ala Ser Asp His Val Tyr Lys Gly Cys Phe Asp
        130                 135                 140

Gly Asn Val Thr Leu Thr Ala Ala Asn Val Thr Val Ser Leu Pro Val
145                 150                 155                 160

Arg Gly Cys Val Gln Asp Glu Phe Cys Thr Arg Asp Gly Val Thr Gly
                165                 170                 175

Pro Gly Phe Thr Leu Ser Gly Ser Cys Cys Gln Gly Ser Arg Cys Asn
                180                 185                 190

Ser Asp Leu Arg Asn Lys Thr Tyr Phe Ser Pro Arg Ile Pro Pro Leu
        195                 200                 205

Val Arg Leu Pro Pro Glu Pro Thr Thr Val Ala Ser Thr Thr Ser
210                 215                 220

Val Thr Thr Ser Thr Ser Ala Pro Val Arg Pro Thr Ser Thr Thr Lys
225                 230                 235                 240

Pro Met Pro Ala Pro
            245

<210> SEQ ID NO 8
<211> LENGTH: 200
<212> TYPE: PRT
<213> ORGANISM: Homo sapiens

<400> SEQUENCE: 8

Leu Glu Cys Tyr Ser Cys Val Gln Lys Ala Asp Asp Gly Cys Ser Pro
1               5                   10                  15

Asn Lys Met Lys Thr Val Lys Cys Ala Pro Gly Val Asp Val Cys Thr
            20                  25                  30

Glu Ala Val Gly Ala Val Glu Thr Ile His Gly Gln Phe Ser Leu Ala
        35                  40                  45

Val Arg Gly Cys Gly Ser Gly Leu Pro Gly Lys Asn Asp Arg Gly Leu
    50                  55                  60

Asp Leu His Gly Leu Leu Ala Phe Ile Gln Leu Gln Cys Ala Gln
65                  70                  75                  80

Asp Arg Cys Asn Ala Lys Leu Asn Leu Thr Ser Arg Ala Leu Asp Pro
                85                  90                  95

Ala Gly Asn Glu Ser Ala Tyr Pro Pro Asn Gly Val Glu Cys Tyr Ser
            100                 105                 110

Cys Val Gly Leu Ser Arg Glu Ala Cys Gln Gly Thr Ser Pro Pro Val
        115                 120                 125

Val Ser Cys Tyr Asn Ala Ser Asp His Val Tyr Lys Gly Cys Phe Asp
    130                 135                 140

Gly Asn Val Thr Leu Thr Ala Ala Asn Val Thr Val Ser Leu Pro Val
145                 150                 155                 160

Arg Gly Cys Val Gln Asp Glu Phe Cys Thr Arg Asp Gly Val Thr Gly
                165                 170                 175

Pro Gly Phe Thr Leu Ser Gly Ser Cys Cys Gln Gly Ser Arg Cys Asn
            180                 185                 190

Ser Asp Leu Arg Asn Lys Thr Tyr
        195                 200

<210> SEQ ID NO 9
<211> LENGTH: 190
<212> TYPE: PRT
<213> ORGANISM: Homo sapiens

<400> SEQUENCE: 9
```

```
Cys Val Gln Lys Ala Asp Asp Gly Cys Ser Pro Asn Lys Met Lys Thr
1               5                   10                  15

Val Lys Cys Ala Pro Gly Val Asp Val Cys Thr Glu Ala Val Gly Ala
            20                  25                  30

Val Glu Thr Ile His Gly Gln Phe Ser Leu Ala Val Arg Gly Cys Gly
        35                  40                  45

Ser Gly Leu Pro Gly Lys Asn Asp Arg Gly Leu Asp Leu His Gly Leu
50                  55                  60

Leu Ala Phe Ile Gln Leu Gln Gln Cys Ala Gln Asp Arg Cys Asn Ala
65                  70                  75                  80

Lys Leu Asn Leu Thr Ser Arg Ala Leu Asp Pro Ala Gly Asn Glu Ser
                85                  90                  95

Ala Tyr Pro Pro Asn Gly Val Glu Cys Tyr Ser Cys Val Gly Leu Ser
            100                 105                 110

Arg Glu Ala Cys Gln Gly Thr Ser Pro Pro Val Val Ser Cys Tyr Asn
        115                 120                 125

Ala Ser Asp His Val Tyr Lys Gly Cys Phe Asp Gly Asn Val Thr Leu
130                 135                 140

Thr Ala Ala Asn Val Thr Val Ser Leu Pro Val Arg Gly Cys Val Gln
145                 150                 155                 160

Asp Glu Phe Cys Thr Arg Asp Gly Val Thr Gly Pro Gly Phe Thr Leu
                165                 170                 175

Ser Gly Ser Cys Cys Gln Gly Ser Arg Cys Asn Ser Asp Leu
            180                 185                 190

<210> SEQ ID NO 10
<211> LENGTH: 180
<212> TYPE: PRT
<213> ORGANISM: Homo sapiens

<400> SEQUENCE: 10

Thr Val Lys Cys Ala Pro Gly Val Asp Val Cys Thr Glu Ala Val Gly
1               5                   10                  15

Ala Val Glu Thr Ile His Gly Gln Phe Ser Leu Ala Val Arg Gly Cys
            20                  25                  30

Gly Ser Gly Leu Pro Gly Lys Asn Asp Arg Gly Leu Asp Leu His Gly
        35                  40                  45

Leu Leu Ala Phe Ile Gln Leu Gln Gln Cys Ala Gln Asp Arg Cys Asn
50                  55                  60

Ala Lys Leu Asn Leu Thr Ser Arg Ala Leu Asp Pro Ala Gly Asn Glu
65                  70                  75                  80

Ser Ala Tyr Pro Pro Asn Gly Val Glu Cys Tyr Ser Cys Val Gly Leu
                85                  90                  95

Ser Arg Glu Ala Cys Gln Gly Thr Ser Pro Pro Val Val Ser Cys Tyr
            100                 105                 110

Asn Ala Ser Asp His Val Tyr Lys Gly Cys Phe Asp Gly Asn Val Thr
        115                 120                 125

Leu Thr Ala Ala Asn Val Thr Val Ser Leu Pro Val Arg Gly Cys Val
130                 135                 140

Gln Asp Glu Phe Cys Thr Arg Asp Gly Val Thr Gly Pro Gly Phe Thr
145                 150                 155                 160

Leu Ser Gly Ser Cys Cys Gln Gly Ser Arg Cys Asn Ser Asp Leu Arg
                165                 170                 175

Asn Lys Thr Tyr
```

<210> SEQ ID NO 11
<211> LENGTH: 165
<212> TYPE: PRT
<213> ORGANISM: Homo sapiens

<400> SEQUENCE: 11

Thr Val Lys Cys Ala Pro Gly Val Asp Val Cys Thr Glu Ala Val Gly
1               5                   10                  15

Ala Val Glu Thr Ile His Gly Gln Phe Ser Leu Ala Val Arg Gly Cys
            20                  25                  30

Gly Ser Gly Leu Pro Gly Lys Asn Asp Arg Gly Leu Asp Leu His Gly
        35                  40                  45

Leu Leu Ala Phe Ile Gln Leu Gln Gln Cys Ala Gln Asp Arg Cys Asn
    50                  55                  60

Ala Lys Leu Asn Leu Thr Ser Arg Ala Leu Asp Pro Ala Gly Asn Glu
65                  70                  75                  80

Ser Ala Tyr Pro Pro Asn Gly Val Glu Cys Tyr Ser Cys Val Gly Leu
                85                  90                  95

Ser Arg Glu Ala Cys Gln Gly Thr Ser Pro Val Val Ser Cys Tyr
            100                 105                 110

Asn Ala Ser Asp His Val Tyr Lys Gly Cys Phe Asp Gly Asn Val Thr
        115                 120                 125

Leu Thr Ala Ala Asn Val Thr Val Ser Leu Pro Val Arg Gly Cys Val
    130                 135                 140

Gln Asp Glu Phe Cys Thr Arg Asp Gly Val Thr Gly Pro Gly Phe Thr
145                 150                 155                 160

Leu Ser Gly Ser Cys
                165

<210> SEQ ID NO 12
<211> LENGTH: 140
<212> TYPE: PRT
<213> ORGANISM: Homo sapiens

<400> SEQUENCE: 12

Leu Glu Cys Tyr Ser Cys Val Gln Lys Ala Asp Asp Gly Cys Ser Pro
1               5                   10                  15

Asn Lys Met Lys Thr Val Lys Cys Ala Pro Gly Val Asp Val Cys Thr
            20                  25                  30

Glu Ala Val Gly Ala Val Glu Thr Ile His Gly Gln Phe Ser Leu Ala
        35                  40                  45

Val Arg Gly Cys Gly Ser Gly Leu Pro Gly Lys Asn Asp Arg Gly Leu
    50                  55                  60

Asp Leu His Gly Leu Leu Ala Phe Ile Gln Leu Gln Gln Cys Ala Gln
65                  70                  75                  80

Asp Arg Cys Asn Ala Lys Leu Asn Leu Thr Ser Arg Ala Leu Asp Pro
                85                  90                  95

Ala Gly Asn Glu Ser Ala Tyr Pro Pro Asn Gly Val Glu Cys Tyr Ser
            100                 105                 110

Cys Val Gly Leu Ser Arg Glu Ala Cys Gln Gly Thr Ser Pro Pro Val
        115                 120                 125

Val Ser Cys Tyr Asn Ala Ser Asp His Val Tyr Lys
    130                 135                 140

-continued

<210> SEQ ID NO 13
<211> LENGTH: 125
<212> TYPE: PRT
<213> ORGANISM: Homo sapiens

<400> SEQUENCE: 13

```
Pro Asn Lys Met Lys Thr Val Lys Cys Ala Pro Gly Val Asp Val Cys
1               5                   10                  15

Thr Glu Ala Val Gly Ala Val Glu Thr Ile His Gly Gln Phe Ser Leu
            20                  25                  30

Ala Val Arg Gly Cys Gly Ser Gly Leu Pro Gly Lys Asn Asp Arg Gly
        35                  40                  45

Leu Asp Leu His Gly Leu Leu Ala Phe Ile Gln Leu Gln Gln Cys Ala
    50                  55                  60

Gln Asp Arg Cys Asn Ala Lys Leu Asn Leu Thr Ser Arg Ala Leu Asp
65                  70                  75                  80

Pro Ala Gly Asn Glu Ser Ala Tyr Pro Pro Asn Gly Val Glu Cys Tyr
                85                  90                  95

Ser Cys Val Gly Leu Ser Arg Glu Ala Cys Gln Gly Thr Ser Pro Pro
            100                 105                 110

Val Val Ser Cys Tyr Asn Ala Ser Asp His Val Tyr Lys
        115                 120                 125
```

<210> SEQ ID NO 14
<211> LENGTH: 120
<212> TYPE: PRT
<213> ORGANISM: Homo sapiens

<400> SEQUENCE: 14

```
Leu Glu Cys Tyr Ser Cys Val Gln Lys Ala Asp Asp Gly Cys Ser Pro
1               5                   10                  15

Asn Lys Met Lys Thr Val Lys Cys Ala Pro Gly Val Asp Val Cys Thr
            20                  25                  30

Glu Ala Val Gly Ala Val Glu Thr Ile His Gly Gln Phe Ser Leu Ala
        35                  40                  45

Val Arg Gly Cys Gly Ser Gly Leu Pro Gly Lys Asn Asp Arg Gly Leu
    50                  55                  60

Asp Leu His Gly Leu Leu Ala Phe Ile Gln Leu Gln Gln Cys Ala Gln
65                  70                  75                  80

Asp Arg Cys Asn Ala Lys Leu Asn Leu Thr Ser Arg Ala Leu Asp Pro
                85                  90                  95

Ala Gly Asn Glu Ser Ala Tyr Pro Pro Asn Gly Val Glu Cys Tyr Ser
            100                 105                 110

Cys Val Gly Leu Ser Arg Glu Ala
        115                 120
```

<210> SEQ ID NO 15
<211> LENGTH: 110
<212> TYPE: PRT
<213> ORGANISM: Homo sapiens

<400> SEQUENCE: 15

```
Cys Thr Glu Ala Val Gly Ala Val Glu Thr Ile His Gly Gln Phe Ser
1               5                   10                  15

Leu Ala Val Arg Gly Cys Gly Ser Gly Leu Pro Gly Lys Asn Asp Arg
            20                  25                  30

Gly Leu Asp Leu His Gly Leu Leu Ala Phe Ile Gln Leu Gln Gln Cys
        35                  40                  45
```

Ala Gln Asp Arg Cys Asn Ala Lys Leu Asn Leu Thr Ser Arg Ala Leu
          50                  55                  60

Asp Pro Ala Gly Asn Glu Ser Ala Tyr Pro Pro Asn Gly Val Glu Cys
65                  70                  75                  80

Tyr Ser Cys Val Gly Leu Ser Arg Glu Ala Cys Gln Gly Thr Ser Pro
                85                  90                  95

Pro Val Val Ser Cys Tyr Asn Ala Ser Asp His Val Tyr Lys
            100                 105                 110

<210> SEQ ID NO 16
<211> LENGTH: 100
<212> TYPE: PRT
<213> ORGANISM: Homo sapiens

<400> SEQUENCE: 16

Cys Val Gln Lys Ala Asp Asp Gly Cys Ser Pro Asn Lys Met Lys Thr
1               5                   10                  15

Val Lys Cys Ala Pro Gly Val Asp Val Cys Thr Glu Ala Val Gly Ala
                20                  25                  30

Val Glu Thr Ile His Gly Gln Phe Ser Leu Ala Val Arg Gly Cys Gly
            35                  40                  45

Ser Gly Leu Pro Gly Lys Asn Asp Arg Gly Leu Asp Leu His Gly Leu
        50                  55                  60

Leu Ala Phe Ile Gln Leu Gln Gln Cys Ala Gln Asp Arg Cys Asn Ala
65                  70                  75                  80

Lys Leu Asn Leu Thr Ser Arg Ala Leu Asp Pro Ala Gly Asn Glu Ser
                85                  90                  95

Ala Tyr Pro Pro
            100

<210> SEQ ID NO 17
<211> LENGTH: 187
<212> TYPE: PRT
<213> ORGANISM: Homo sapiens

<400> SEQUENCE: 17

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Lys Pro
                20                  25                  30

Asp Glu Thr Leu Thr Leu Thr Cys Thr Val Ser Gly Phe Ser Leu Asn
            35                  40                  45

Thr Val Ala Ile Ser Trp Val Arg Gln Ala Pro Gly Lys Gly Leu Glu
        50                  55                  60

Trp Ile Gly Phe Ile His Pro Thr Val Asn Thr Tyr Tyr Ala Arg Trp
65                  70                  75                  80

Ala Lys Gly Arg Phe Thr Ile Ser Arg Ala Ser Ser Thr Thr Val Asp
                85                  90                  95

Leu Lys Val Thr Ser Leu Thr Phe Glu Asp Ala Ala Thr Tyr Phe Cys
            100                 105                 110

Val Arg Gly Asn Ala His Tyr Asp Ile Trp Gly Pro Gly Thr Leu Val
        115                 120                 125

Thr Val Ser Leu Gly Gln Pro Lys Ala Pro Ser Val Phe Pro Leu Ala
    130                 135                 140

Pro Cys Cys Gly Asp Thr Pro Ser Ser Thr Val Thr Leu Gly Cys Leu
145                 150                 155                 160

Val Lys Gly Tyr Leu Pro Glu Pro Val Thr Val Thr Trp Asn Ser Gly
                165                 170                 175

Thr Leu Thr Asn Gly Val Arg Thr Phe Pro Ser
            180                 185

<210> SEQ ID NO 18
<211> LENGTH: 176
<212> TYPE: PRT
<213> ORGANISM: Homo sapiens

<400> SEQUENCE: 18

Met Asp Thr Arg Ala Pro Thr Gln Leu Gly Leu Leu Leu Leu Leu Trp
1               5                   10                  15

Leu Pro Gly Ala Arg Cys Ala Phe Glu Leu Thr Gln Thr Pro Ser Leu
            20                  25                  30

Val Ser Ala Ala Val Gly Gly Thr Val Thr Ile Ser Cys Gln Ser Ser
        35                  40                  45

Gln Ser Val Tyr Ser Asp Asn Tyr Leu Ala Trp Tyr Gln Gln Lys Pro
    50                  55                  60

Gly Gln Arg Pro Lys Leu Leu Ile Tyr Lys Ala Ser Asp Leu Ala Ser
65                  70                  75                  80

Gly Val Pro Ser Arg Phe Lys Gly Ser Gly Ser Gly Thr Glu Phe Thr
                85                  90                  95

Leu Thr Ile Ser Asp Leu Glu Cys Ala Asp Ala Ala Thr Tyr Tyr Cys
            100                 105                 110

Gln Ser Tyr Tyr Gly Val Ser Ser Asp Ser Asn Ala Phe Gly Gly Gly
        115                 120                 125

Thr Glu Val Val Val Lys Gly Asp Pro Val Ala Pro Thr Val Leu Ile
    130                 135                 140

Phe Pro Pro Ser Ala Asp Leu Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

<210> SEQ ID NO 19
<211> LENGTH: 194
<212> TYPE: PRT
<213> ORGANISM: Homo sapiens

<400> SEQUENCE: 19

Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Gly Leu Val Lys
            20                  25                  30

Pro Gly Gly Thr Leu Thr Leu Thr Cys Thr Ala Ser Gly Phe Ser Leu
        35                  40                  45

Ile Ser Thr Tyr Tyr Ile Cys Trp Val Arg Gln Ala Pro Gly Lys Gly
    50                  55                  60

Leu Glu Trp Ile Gly Cys Ile Pro Leu Ser His Ser Val Ser Trp Tyr
65                  70                  75                  80

Ala Asn Trp Val Asn Gly Arg Phe Ser Ile Ser Lys Thr Ser Ser Thr
                85                  90                  95

Thr Val Thr Leu Lys Met Ala Ser Leu Thr Asp Ala Asp Thr Ala Thr
            100                 105                 110

Tyr Phe Cys Gly Arg Gly Ser Ser Gly Trp Gly Val Asp Ser Lys Leu
        115                 120                 125

Trp Gly Pro Gly Thr Leu Val Thr Val Ser Ser Gly Gln Pro Lys Ala
            130                 135                 140

Pro Ser Val Phe Pro Leu Ala Pro Cys Cys Gly Asp Thr Pro Ser Ser
145                 150                 155                 160

Thr Val Thr Leu Gly Cys Leu Val Lys Gly Tyr Leu Pro Glu Pro Val
                165                 170                 175

Thr Val Thr Trp Asn Ser Gly Thr Leu Thr Asn Gly Val Arg Thr Phe
                180                 185                 190

Pro Ser

<210> SEQ ID NO 20
<211> LENGTH: 174
<212> TYPE: PRT
<213> ORGANISM: Homo sapiens

<400> SEQUENCE: 20

Met Asp Thr Arg Ala Pro Thr Gln Leu Leu Gly Leu Leu Leu Leu Trp
1               5                   10                  15

Leu Pro Gly Ala Pro Phe Ala Ala Val Leu Thr Gln Thr Pro Ser Pro
                20                  25                  30

Val Ser Ala Ser Val Gly Gly Thr Val Thr Ile Asn Cys Gln Ser Ser
            35                  40                  45

Pro Ser Val Ala Ser Gly Tyr Leu Ser Trp Phe Gln Gln Lys Pro Gly
        50                  55                  60

Gln Pro Pro Lys Leu Leu Ile Tyr Arg Ala Ser Thr Leu Val Ser Gly
65                  70                  75                  80

Val Pro Ser Arg Phe Lys Gly Ser Gly Ser Gly Thr His Phe Thr Leu
                85                  90                  95

Thr Ile Ser Asp Val Gln Cys Asp Asp Ala Ala Thr Tyr Tyr Cys Ala
                100                 105                 110

Gly Ala Tyr Ser Ser Arg Ser Asp Thr Thr Phe Gly Gly Gly Thr Glu
            115                 120                 125

Val Val Val Lys Gly Asp Pro Val Ala Pro Thr Val Leu Ile Phe Pro
130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val
                165                 170

<210> SEQ ID NO 21
<211> LENGTH: 19
<212> TYPE: PRT
<213> ORGANISM: Homo sapiens

<400> SEQUENCE: 21

Met Glu Thr Gly Leu Arg Trp Leu Leu Leu Val Ala Val Leu Lys Gly
1               5                   10                  15

Val Gln Cys

<210> SEQ ID NO 22
<211> LENGTH: 29
<212> TYPE: PRT
<213> ORGANISM: Homo sapiens

<400> SEQUENCE: 22

Gln Ser Leu Glu Glu Ser Gly Gly Arg Leu Val Lys Pro Asp Glu Thr
1               5                   10                  15

```
Leu Thr Leu Thr Cys Thr Val Ser Gly Phe Ser Leu Asn
            20                  25

<210> SEQ ID NO 23
<211> LENGTH: 5
<212> TYPE: PRT
<213> ORGANISM: Homo sapiens

<400> SEQUENCE: 23

Thr Val Ala Ile Ser
1               5

<210> SEQ ID NO 24
<211> LENGTH: 14
<212> TYPE: PRT
<213> ORGANISM: Homo sapiens

<400> SEQUENCE: 24

Trp Val Arg Gln Ala Pro Gly Lys Gly Leu Glu Trp Ile Gly
1               5                   10

<210> SEQ ID NO 25
<211> LENGTH: 16
<212> TYPE: PRT
<213> ORGANISM: Homo sapiens

<400> SEQUENCE: 25

Phe Ile His Pro Thr Val Asn Thr Tyr Tyr Ala Arg Trp Ala Lys Gly
1               5                   10                  15

<210> SEQ ID NO 26
<211> LENGTH: 31
<212> TYPE: PRT
<213> ORGANISM: Homo sapiens

<400> SEQUENCE: 26

Arg Phe Thr Ile Ser Arg Ala Ser Ser Thr Thr Val Asp Leu Lys Val
1               5                   10                  15

Thr Ser Leu Thr Phe Glu Asp Ala Ala Thr Tyr Phe Cys Val Arg
            20                  25                  30

<210> SEQ ID NO 27
<211> LENGTH: 7
<212> TYPE: PRT
<213> ORGANISM: Homo sapiens

<400> SEQUENCE: 27

Gly Asn Ala His Tyr Asp Ile
1               5

<210> SEQ ID NO 28
<211> LENGTH: 11
<212> TYPE: PRT
<213> ORGANISM: Homo sapiens

<400> SEQUENCE: 28

Trp Gly Pro Gly Thr Leu Val Thr Val Ser Leu
1               5                   10

<210> SEQ ID NO 29
<211> LENGTH: 22
<212> TYPE: PRT
<213> ORGANISM: Homo sapiens
```

```
<400> SEQUENCE: 29

Met Asp Thr Arg Ala Pro Thr Gln Leu Leu Gly Leu Leu Leu Leu Trp
1               5                   10                  15

Leu Pro Gly Ala Arg Cys
            20

<210> SEQ ID NO 30
<211> LENGTH: 23
<212> TYPE: PRT
<213> ORGANISM: Homo sapiens

<400> SEQUENCE: 30

Ala Phe Glu Leu Thr Gln Thr Pro Ser Leu Val Ser Ala Ala Val Gly
1               5                   10                  15

Gly Thr Val Thr Ile Ser Cys
            20

<210> SEQ ID NO 31
<211> LENGTH: 13
<212> TYPE: PRT
<213> ORGANISM: Homo sapiens

<400> SEQUENCE: 31

Gln Ser Ser Gln Ser Val Tyr Ser Asp Asn Tyr Leu Ala
1               5                   10

<210> SEQ ID NO 32
<211> LENGTH: 15
<212> TYPE: PRT
<213> ORGANISM: Homo sapiens

<400> SEQUENCE: 32

Trp Tyr Gln Gln Lys Pro Gly Gln Arg Pro Lys Leu Leu Ile Tyr
1               5                   10                  15

<210> SEQ ID NO 33
<211> LENGTH: 7
<212> TYPE: PRT
<213> ORGANISM: Homo sapiens

<400> SEQUENCE: 33

Lys Ala Ser Asp Leu Ala Ser
1               5

<210> SEQ ID NO 34
<211> LENGTH: 32
<212> TYPE: PRT
<213> ORGANISM: Homo sapiens

<400> SEQUENCE: 34

Gly Val Pro Ser Arg Phe Lys Gly Ser Gly Ser Gly Thr Glu Phe Thr
1               5                   10                  15

Leu Thr Ile Ser Asp Leu Glu Cys Ala Asp Ala Ala Thr Tyr Tyr Cys
            20                  25                  30

<210> SEQ ID NO 35
<211> LENGTH: 12
<212> TYPE: PRT
<213> ORGANISM: Homo sapiens

<400> SEQUENCE: 35

Gln Ser Tyr Tyr Gly Val Ser Asp Ser Asn Ala
1               5                   10
```

```
<210> SEQ ID NO 36
<211> LENGTH: 10
<212> TYPE: PRT
<213> ORGANISM: Homo sapiens

<400> SEQUENCE: 36

Phe Gly Gly Gly Thr Glu Val Val Val Lys
1               5                   10

<210> SEQ ID NO 37
<211> LENGTH: 19
<212> TYPE: PRT
<213> ORGANISM: Homo sapiens

<400> SEQUENCE: 37

Met Glu Thr Gly Leu Arg Trp Leu Leu Leu Val Ala Val Leu Lys Gly
1               5                   10                  15

Val Gln Cys

<210> SEQ ID NO 38
<211> LENGTH: 30
<212> TYPE: PRT
<213> ORGANISM: Homo sapiens

<400> SEQUENCE: 38

Gln Glu Gln Leu Glu Glu Ser Gly Gly Gly Leu Val Lys Pro Gly Gly
1               5                   10                  15

Thr Leu Thr Leu Thr Cys Thr Ala Ser Gly Phe Ser Leu Ile
            20                  25                  30

<210> SEQ ID NO 39
<211> LENGTH: 6
<212> TYPE: PRT
<213> ORGANISM: Homo sapiens

<400> SEQUENCE: 39

Ser Thr Tyr Tyr Ile Cys
1               5

<210> SEQ ID NO 40
<211> LENGTH: 14
<212> TYPE: PRT
<213> ORGANISM: Homo sapiens

<400> SEQUENCE: 40

Trp Val Arg Gln Ala Pro Gly Lys Gly Leu Glu Trp Ile Gly
1               5                   10

<210> SEQ ID NO 41
<211> LENGTH: 17
<212> TYPE: PRT
<213> ORGANISM: Homo sapiens

<400> SEQUENCE: 41

Cys Ile Pro Leu Ser His Ser Val Ser Trp Tyr Ala Asn Trp Val Asn
1               5                   10                  15

Gly

<210> SEQ ID NO 42
<211> LENGTH: 31
<212> TYPE: PRT
<213> ORGANISM: Homo sapiens
```

```
<400> SEQUENCE: 42

Arg Phe Ser Ile Ser Lys Thr Ser Ser Thr Thr Val Thr Leu Lys Met
1               5                   10                  15

Ala Ser Leu Thr Asp Ala Asp Thr Ala Thr Tyr Phe Cys Gly Arg
            20                  25                  30

<210> SEQ ID NO 43
<211> LENGTH: 11
<212> TYPE: PRT
<213> ORGANISM: Homo sapiens

<400> SEQUENCE: 43

Gly Ser Ser Gly Trp Gly Val Asp Ser Lys Leu
1               5                   10

<210> SEQ ID NO 44
<211> LENGTH: 11
<212> TYPE: PRT
<213> ORGANISM: Homo sapiens

<400> SEQUENCE: 44

Trp Gly Pro Gly Thr Leu Val Thr Val Ser Ser
1               5                   10

<210> SEQ ID NO 45
<211> LENGTH: 23
<212> TYPE: PRT
<213> ORGANISM: Homo sapiens

<400> SEQUENCE: 45

Met Asp Thr Arg Ala Pro Thr Gln Leu Leu Gly Leu Leu Leu Leu Trp
1               5                   10                  15

Leu Pro Gly Ala Pro Phe Ala
            20

<210> SEQ ID NO 46
<211> LENGTH: 22
<212> TYPE: PRT
<213> ORGANISM: Homo sapiens

<400> SEQUENCE: 46

Ala Val Leu Thr Gln Thr Pro Ser Pro Val Ser Ala Ser Val Gly Gly
1               5                   10                  15

Thr Val Thr Ile Asn Cys
            20

<210> SEQ ID NO 47
<211> LENGTH: 12
<212> TYPE: PRT
<213> ORGANISM: Homo sapiens

<400> SEQUENCE: 47

Gln Ser Ser Pro Ser Val Ala Ser Gly Tyr Leu Ser
1               5                   10

<210> SEQ ID NO 48
<211> LENGTH: 15
<212> TYPE: PRT
<213> ORGANISM: Homo sapiens

<400> SEQUENCE: 48

Trp Phe Gln Gln Lys Pro Gly Gln Pro Pro Lys Leu Leu Ile Tyr
```

<210> SEQ ID NO 49
<211> LENGTH: 7
<212> TYPE: PRT
<213> ORGANISM: Homo sapiens

<400> SEQUENCE: 49

Arg Ala Ser Thr Leu Val Ser
1               5

<210> SEQ ID NO 50
<211> LENGTH: 32
<212> TYPE: PRT
<213> ORGANISM: Homo sapiens

<400> SEQUENCE: 50

Gly Val Pro Ser Arg Phe Lys Gly Ser Gly Ser Gly Thr His Phe Thr
1               5                   10                  15

Leu Thr Ile Ser Asp Val Gln Cys Asp Asp Ala Ala Thr Tyr Tyr Cys
            20                  25                  30

<210> SEQ ID NO 51
<211> LENGTH: 11
<212> TYPE: PRT
<213> ORGANISM: Homo sapiens

<400> SEQUENCE: 51

Ala Gly Ala Tyr Ser Ser Arg Ser Asp Thr Thr
1               5                   10

<210> SEQ ID NO 52
<211> LENGTH: 10
<212> TYPE: PRT
<213> ORGANISM: Homo sapiens

<400> SEQUENCE: 52

Phe Gly Gly Gly Thr Glu Val Val Val Lys
1               5                   10

<210> SEQ ID NO 53
<211> LENGTH: 94
<212> TYPE: PRT
<213> ORGANISM: Homo sapiens

<400> SEQUENCE: 53

Cys Tyr Ser Cys Val Gln Lys Ala Asp Asp Gly Cys Ser Pro Asn Lys
1               5                   10                  15

Met Lys Thr Val Lys Cys Ala Pro Gly Val Asp Val Cys Thr Glu Ala
            20                  25                  30

Val Gly Ala Val Glu Thr Ile His Gly Gln Phe Ser Leu Ala Val Arg
        35                  40                  45

Gly Cys Gly Ser Gly Leu Pro Gly Lys Asn Asp Arg Gly Leu Asp Leu
    50                  55                  60

His Gly Leu Leu Ala Phe Ile Gln Leu Gln Gln Cys Ala Gln Asp Arg
65                  70                  75                  80

Cys Asn Ala Lys Leu Asn Leu Thr Ser Arg Ala Leu Asp Pro
                85                  90

<210> SEQ ID NO 54
<211> LENGTH: 55
<212> TYPE: PRT

<213> ORGANISM: Homo sapiens

<400> SEQUENCE: 54

Pro Asn Lys Met Lys Thr Val Lys Cys Ala Pro Gly Val Asp Val Cys
1               5                   10                  15
Thr Glu Ala Val Gly Ala Val Glu Thr Ile His Gly Gln Phe Ser Leu
            20                  25                  30
Ala Val Arg Gly Cys Gly Ser Gly Leu Pro Gly Lys Asn Asp Arg Gly
        35                  40                  45
Leu Asp Leu His Gly Leu Leu
    50                  55

<210> SEQ ID NO 55
<211> LENGTH: 47
<212> TYPE: PRT
<213> ORGANISM: Homo sapiens

<400> SEQUENCE: 55

Lys Thr Val Lys Cys Ala Pro Gly Val Asp Val Cys Thr Glu Ala Val
1               5                   10                  15
Gly Ala Val Glu Thr Ile His Gly Gln Phe Ser Leu Ala Val Arg Gly
            20                  25                  30
Cys Gly Ser Gly Leu Pro Gly Lys Asn Asp Arg Gly Leu Asp Leu
        35                  40                  45

<210> SEQ ID NO 56
<211> LENGTH: 97
<212> TYPE: PRT
<213> ORGANISM: Homo sapiens

<400> SEQUENCE: 56

Tyr Ser Cys Val Gln Lys Ala Asp Asp Gly Cys Ser Pro Asn Lys Met
1               5                   10                  15
Lys Thr Val Lys Cys Ala Pro Gly Val Asp Val Cys Thr Glu Ala Val
            20                  25                  30
Gly Ala Val Glu Thr Ile His Gly Gln Phe Ser Leu Ala Val Arg Gly
        35                  40                  45
Cys Gly Ser Gly Leu Pro Gly Lys Asn Asp Arg Gly Leu Asp Leu His
    50                  55                  60
Gly Leu Leu Ala Phe Ile Gln Leu Gln Gln Cys Ala Gln Asp Arg Cys
65                  70                  75                  80
Asn Ala Lys Leu Asn Leu Thr Ser Arg Ala Leu Asp Pro Ala Gly Asn
                85                  90                  95
Glu

<210> SEQ ID NO 57
<211> LENGTH: 83
<212> TYPE: PRT
<213> ORGANISM: Homo sapiens

<400> SEQUENCE: 57

Cys Tyr Ser Cys Val Gly Leu Ser Arg Glu Ala Cys Gln Gly Thr Ser
1               5                   10                  15
Pro Pro Val Val Ser Cys Tyr Asn Ala Ser Asp His Val Tyr Lys Gly
            20                  25                  30
Cys Phe Asp Gly Asn Val Thr Leu Thr Ala Ala Asn Val Thr Val Ser
        35                  40                  45
Leu Pro Val Arg Gly Cys Val Gln Asp Glu Phe Cys Thr Arg Asp Gly

```
                50                  55                  60
Val Thr Gly Pro Gly Phe Thr Leu Ser Gly Ser Cys Cys Gln Gly Ser
 65                  70                  75                  80

Arg Cys Asn
```

<210> SEQ ID NO 58
<211> LENGTH: 84
<212> TYPE: PRT
<213> ORGANISM: Homo sapiens

<400> SEQUENCE: 58

```
Glu Cys Tyr Ser Cys Val Gly Leu Ser Arg Glu Ala Cys Gln Gly Thr
 1               5                  10                  15

Ser Pro Pro Val Val Ser Cys Tyr Asn Ala Ser Asp His Val Tyr Lys
                20                  25                  30

Gly Cys Phe Asp Gly Asn Val Thr Leu Thr Ala Ala Asn Val Thr Val
                35                  40                  45

Ser Leu Pro Val Arg Gly Cys Val Gln Asp Glu Phe Cys Thr Arg Asp
                50                  55                  60

Gly Val Thr Gly Pro Gly Phe Thr Leu Ser Gly Ser Cys Cys Gln Gly
 65                  70                  75                  80

Ser Arg Cys Asn
```

<210> SEQ ID NO 59
<211> LENGTH: 71
<212> TYPE: PRT
<213> ORGANISM: Homo sapiens

<400> SEQUENCE: 59

```
Cys Tyr Ser Cys Val Gly Leu Ser Arg Glu Ala Cys Gln Gly Thr Ser
 1               5                  10                  15

Pro Pro Val Val Ser Cys Tyr Asn Ala Ser Asp His Val Tyr Lys Gly
                20                  25                  30

Cys Phe Asp Gly Asn Val Thr Leu Thr Ala Ala Asn Val Thr Val Ser
                35                  40                  45

Leu Pro Val Arg Gly Cys Val Gln Asp Glu Phe Cys Thr Arg Asp Gly
                50                  55                  60

Val Thr Gly Pro Gly Phe Thr
 65                  70
```

<210> SEQ ID NO 60
<211> LENGTH: 73
<212> TYPE: PRT
<213> ORGANISM: Homo sapiens

<400> SEQUENCE: 60

```
Leu Ser Arg Glu Ala Cys Gln Gly Thr Ser Pro Pro Val Val Ser Cys
 1               5                  10                  15

Tyr Asn Ala Ser Asp His Val Tyr Lys Gly Cys Phe Asp Gly Asn Val
                20                  25                  30

Thr Leu Thr Ala Ala Asn Val Thr Val Ser Leu Pro Val Arg Gly Cys
                35                  40                  45

Val Gln Asp Glu Phe Cys Thr Arg Asp Gly Val Thr Gly Pro Gly Phe
                50                  55                  60

Thr Leu Ser Gly Ser Cys Cys Gln Gly
 65                  70
```

```
<210> SEQ ID NO 61
<211> LENGTH: 187
<212> TYPE: PRT
<213> ORGANISM: Artificial Sequence
<220> FEATURE:
<223> OTHER INFORMATION: SEQUENCE AT LEAST 90% IDENTICAL TO SEQ ID NO:
      17
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid
<220> FEATURE:
<221> NAME/KEY: misc_feature
<222> LOCATION: (176)..(176)
<223> OTHER INFORMATION: Xaa can be any naturally occurring amino acid

<400> SEQUENCE: 61

Met Xaa Thr Gly Leu Arg Trp Leu Leu Leu Val Xaa Val Leu Lys Gly
```

```
1               5                   10                  15
Val Gln Cys Gln Ser Leu Glu Xaa Ser Gly Gly Arg Leu Xaa Xaa Pro
            20                  25                  30

Asp Glu Thr Leu Xaa Leu Thr Cys Thr Val Ser Gly Phe Ser Leu Asn
            35                  40                  45

Thr Val Ala Ile Ser Xaa Val Arg Gln Xaa Pro Gly Lys Gly Leu Glu
 50                  55                  60

Trp Ile Gly Phe Ile His Pro Thr Val Asn Thr Tyr Tyr Ala Arg Trp
 65                  70                  75                  80

Xaa Lys Gly Arg Phe Thr Ile Ser Arg Ala Ser Ser Thr Thr Val Xaa
                85                  90                  95

Leu Lys Val Thr Ser Leu Thr Phe Glu Asp Ala Ala Thr Tyr Phe Cys
                100                 105                 110

Val Arg Gly Asn Xaa His Tyr Asp Ile Trp Xaa Pro Gly Thr Leu Val
            115                 120                 125

Thr Val Ser Xaa Gly Gln Pro Lys Ala Pro Ser Val Phe Pro Leu Xaa
 130                 135                 140

Pro Cys Cys Xaa Asp Thr Pro Ser Ser Thr Val Thr Leu Xaa Cys Leu
145                 150                 155                 160

Val Lys Xaa Tyr Leu Pro Glu Pro Val Thr Val Thr Trp Asn Ser Xaa
                165                 170                 175

Thr Leu Thr Asn Gly Val Arg Thr Phe Pro Ser
            180                 185
```

<210> SEQ ID NO 62
<211> LENGTH: 176
<212> TYPE: PRT
<213> ORGANISM: Artificial Sequence
<220> FEATURE:
<223> OTHER INFORMATION: SEQUENCE AT LEAST 80% IDENTICAL TO SEQ ID NO:
      18
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid

```
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (81)..(82)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (120)..(120)
<223> OTHER INFORMATION: Xaa can be any naturally occurring amino acid
<220> FEATURE:
<221> NAME/KEY: misc_feature
<222> LOCATION: (126)..(126)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (139)..(139)
<223> OTHER INFORMATION: Xaa can be any naturally occurring amino acid
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (149)..(150)
<223> OTHER INFORMATION: Xaa can be any naturally occurring amino acid
<220> FEATURE:
<221> NAME/KEY: misc_feature
<222> LOCATION: (153)..(153)
```

-continued

```
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
<222> LOCATION: (175)..(175)
<223> OTHER INFORMATION: Xaa can be any naturally occurring amino acid

<400> SEQUENCE: 62

Met Xaa Thr Arg Ala Pro Thr Gln Xaa Leu Gly Leu Leu Xaa Leu Trp
1               5                   10                  15

Xaa Pro Xaa Ala Arg Cys Xaa Phe Glu Leu Thr Gln Thr Pro Ser Leu
            20                  25                  30

Val Ser Xaa Ala Val Gly Xaa Thr Val Thr Ile Ser Cys Gln Ser Xaa
        35                  40                  45

Gln Ser Val Tyr Ser Xaa Asn Tyr Leu Ala Xaa Tyr Gln Gln Lys Pro
    50                  55                  60

Xaa Gln Arg Pro Lys Xaa Leu Ile Tyr Lys Xaa Ser Xaa Leu Xaa Ser
65                  70                  75                  80

Xaa Xaa Pro Ser Arg Phe Lys Xaa Ser Gly Ser Xaa Thr Xaa Phe Thr
                85                  90                  95

Leu Thr Ile Ser Asp Leu Glu Cys Ala Asp Ala Xaa Thr Tyr Xaa Cys
            100                 105                 110

Gln Ser Tyr Tyr Gly Val Ser Xaa Asp Ser Asn Ala Phe Xaa Gly Gly
        115                 120                 125

Thr Glu Val Xaa Val Lys Gly Asp Pro Val Xaa Pro Thr Val Leu Ile
    130                 135                 140

Phe Pro Xaa Ser Xaa Xaa Leu Val Xaa Thr Gly Thr Val Xaa Ile Val
145                 150                 155                 160

Cys Val Xaa Asn Lys Tyr Phe Pro Asp Val Thr Val Xaa Trp Xaa Val
                165                 170                 175

<210> SEQ ID NO 63
<211> LENGTH: 194
<212> TYPE: PRT
<213> ORGANISM: Artificial Sequence
<220> FEATURE:
<223> OTHER INFORMATION: SEQUENCE AT LEAST 95% IDENTICAL TO SEQ ID NO:
      19
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
```

```
<222> LOCATION: (81)..(81)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (151)..(151)
<223> OTHER INFORMATION: Xaa can be any naturally occurring amino acid

<400> SEQUENCE: 63

Met Glu Thr Gly Leu Arg Trp Leu Leu Leu Val Xaa Val Leu Lys Gly
 1               5                  10                  15

Val Gln Cys Gln Glu Xaa Leu Glu Xaa Ser Gly Gly Gly Leu Val Lys
            20                  25                  30

Pro Gly Gly Thr Leu Thr Leu Thr Cys Thr Ala Ser Xaa Phe Ser Leu
        35                  40                  45

Ile Ser Thr Tyr Tyr Ile Cys Trp Val Arg Gln Ala Pro Gly Lys Gly
 50                  55                  60

Leu Glu Trp Ile Gly Cys Ile Pro Leu Ser His Ser Val Ser Trp Tyr
 65                  70                  75                  80

Xaa Asn Trp Val Asn Gly Arg Phe Ser Ile Ser Lys Thr Ser Thr
                85                  90                  95

Xaa Val Thr Leu Lys Met Ala Ser Leu Thr Asp Ala Asp Thr Ala Thr
            100                 105                 110

Tyr Phe Cys Xaa Arg Gly Ser Ser Gly Trp Gly Val Asp Ser Lys Leu
        115                 120                 125

Trp Gly Pro Gly Thr Leu Val Thr Val Xaa Ser Gly Gln Pro Lys Ala
130                 135                 140

Pro Ser Val Phe Pro Leu Xaa Pro Cys Cys Gly Asp Thr Pro Ser Ser
145                 150                 155                 160

Thr Val Thr Leu Gly Cys Leu Val Lys Gly Tyr Leu Pro Glu Pro Val
                165                 170                 175

Thr Val Thr Trp Asn Ser Gly Thr Leu Thr Asn Gly Val Arg Thr Phe
            180                 185                 190

Pro Ser

<210> SEQ ID NO 64
<211> LENGTH: 174
<212> TYPE: PRT
<213> ORGANISM: Artificial Sequence
<220> FEATURE:
<223> OTHER INFORMATION: SEQUENCE AT LEAST 70% IDENTICAL TO SEQ ID NO:
      20
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
```

-continued

```
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (38)..(39)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (74)..(75)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (88)..(89)
<223> OTHER INFORMATION: Xaa can be any naturally occurring amino acid
<220> FEATURE:
<221> NAME/KEY: misc_feature
<222> LOCATION: (103)..(106)
<223> OTHER INFORMATION: Xaa can be any naturally occurring amino acid
<220> FEATURE:
<221> NAME/KEY: misc_feature
<222> LOCATION: (111)..(114)
```

```
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid
<220> FEATURE:
<221> NAME/KEY: misc_feature
<222> LOCATION: (125)..(126)
<223> OTHER INFORMATION: Xaa can be any naturally occurring amino acid
<220> FEATURE:
<221> NAME/KEY: misc_feature
<222> LOCATION: (130)..(131)
<223> OTHER INFORMATION: Xaa can be any naturally occurring amino acid
<220> FEATURE:
<221> NAME/KEY: misc_feature
<222> LOCATION: (136)..(137)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (173)..(174)
<223> OTHER INFORMATION: Xaa can be any naturally occurring amino acid

<400> SEQUENCE: 64

Met Xaa Thr Arg Ala Xaa Thr Gln Leu Leu Gly Leu Xaa Xaa Xaa Trp
1               5                   10                  15

Leu Pro Xaa Ala Pro Xaa Ala Ala Xaa Leu Thr Gln Thr Xaa Ser Pro
            20                  25                  30

Val Xaa Ala Xaa Val Xaa Xaa Thr Val Xaa Ile Asn Xaa Gln Ser Ser
        35                  40                  45

Pro Xaa Val Ala Ser Gly Tyr Leu Ser Xaa Phe Xaa Gln Lys Pro Xaa
    50                  55                  60

Gln Pro Pro Xaa Leu Leu Ile Tyr Arg Xaa Xaa Thr Leu Xaa Ser Gly
65                  70                  75                  80

Xaa Pro Ser Arg Phe Lys Gly Xaa Xaa Ser Gly Thr His Phe Thr Leu
                85                  90                  95

Thr Ile Ser Asp Val Gln Xaa Xaa Xaa Xaa Ala Thr Tyr Tyr Xaa Xaa
```

```
                    100                 105                 110
Xaa Xaa Tyr Ser Ser Arg Xaa Asp Xaa Thr Xaa Gly Xaa Xaa Thr Glu
        115                 120                 125

Val Xaa Xaa Lys Gly Asp Pro Xaa Xaa Pro Thr Xaa Leu Ile Phe Pro
    130                 135             140

Pro Ala Xaa Asp Gln Val Ala Thr Gly Xaa Val Thr Ile Xaa Cys Val
145             150                 155                 160

Ala Xaa Lys Tyr Phe Pro Xaa Val Thr Xaa Thr Trp Xaa Xaa
                165             170
```

ANTIBODIES, COMPOSITIONS, AND IMMUNOHISTOCHEMISTRY METHODS FOR DETECTING C4.4A

CROSS-REFERENCE TO RELATED APPLICATIONS

This is a continuation of PCT/EP2016/058135, filed Apr. 13, 2016, which claims the benefit of U.S. Provisional Patent Application No. 62/149,239, filed Apr. 17, 2015, the content of each of which is incorporated herein by reference in its entirety.

FIELD OF THE INVENTION

The present invention relates to immunohistochemistry assays and reagents, more particularly to antibodies directed to the tumor-associated antigen C4.4a and methods of use, for example for diagnostic use.

BACKGROUND OF THE INVENTION

C4.4a is a protein homologue of the urokinase receptor. It is a GPI (glycosyl-phosphatidylinoditol) binding protein that has a similar structure to urokinase receptor (uPAR) and belongs to Ly-6 family as uPAR. While most of Ly-6 family molecules consist of single domain, uPAR is of three cysteine-rich domains. C4.4A is a membrane protein that binds to cell membranes in GPI binding sites, and consists of two cysteine-rich domains and a cysteine-lacking third domain. C4.4A was isolated from metastatic rat pancreatic cancer cell lines in 1989, and its human homolog was isolated in 2001 (Hansen et al., 2005, Thrombosis and Haemostasis, 93(4):A33, XP009145645). C4.4a is also considered to be a tumor-associated antigen, e.g., in lung cancer, esophageal cancer, cervical cancer, skin cancer, colon cancer, urothelial cancer, etc.

Several polyclonal C4.4a antibodies have been previously produced (e.g., Catalog No. 28073 from Clonetech; Catalog No. NBP2-32598 from Novus; Catalog Nos. LS-A9857, A9856, and LS-C186776 from LifeSpan Biosciences). However, these antibodies do not perform well in immuno-histochemistry (IHC) assays. As of the filing of this application, Inventors are not aware of any other group who has been able to produce a monoclonal C4.4a antibody, e.g., a monoclonal C4.4a antibody that is adapted for IHC assays and/or for diagnostic purposes. One common method of producing monoclonal antibodies is using mouse hybridoma techniques. However, it is not uncommon for hybridomas to lose productivity or for the hybridoma cells to change, resulting in changes in the antibody (and effectiveness of the antibody). And, high sequence similarity between human C4.4a and its rabbit counterpart adds to the difficulty of producing an anti-C4.4a antibody directed to the uPAR-like domain 1 or the uPAR-like domain 2.

U.S. Pat. Application No. 2012/0321619 is directed to C4.4a antibodies. Without wishing to limit the present invention to any theory or mechanism, it appears that the C4.4a antibodies in U.S. Pat. Application No. 2012/0321619 were used for C4.4a detection purposes in cell lines and in other in vitro assays, and these antibodies would not work well in formalin-fixed paraffin-embedded (FFPE) tissue samples, e.g., for diagnostic purposes. Hansen et al. (Biochem J, 2004, 380:845-857) discloses C4.4a antibodies; however, these antibodies are polyclonal antibodies.

SUMMARY OF THE INVENTION

As of the filing of this application, Inventors have not been able to find a monoclonal C4.4a antibody, e.g., a monoclonal C4.4a antibody adapted for IHC assays, e.g., IHC assays in FFPE tissue samples. The present invention features monoclonal C4.4a antibodies, methods of detecting C4.4a using the monoclonal antibodies disclosed herein, as well as methods for detecting C4.4a-associated cancers using the monoclonal C4.4a antibodies disclosed herein. The monoclonal C4.4a antibodies of the present invention can be used to detect C4.4a in FFPE tissue samples.

For example, the present invention features an isolated antibody (e.g., a monoclonal antibody) specific for C4.4a, wherein the antibody binds specifically to a particular sequence or region of C4.4a, e.g., a C4.4a epitope as described herein (e.g., an epitope within the uPAR-like domain 1, an epitope within the uPAR-like domain 2, etc.). In some embodiments, the antibody comprises clone S42H9L5 or clone S20H1L1 as disclosed herein. The present invention also features a monoclonal C4.4a antibody or C4.4a binding fragment, wherein the antibody or binding fragment has the same epitopic specificity as an antibody selected from the group consisting of clone S42H9L5 and clone S20H1L1.

In some embodiments, the C4.4a antibody of the present invention comprises SEQ ID NO: 17, SEQ ID NO: 18, SEQ ID NO: 19, SEQ ID NO: 20, a fragment thereof, a peptide that is at least 60% identical to SEQ ID NO: 17, SEQ ID NO: 18, SEQ ID NO: 19, or SEQ ID NO: 20, a peptide that is at least 60% identical to a fragment of one of SEQ ID NO: 17, SEQ ID NO: 18, SEQ ID NO: 19, or SEQ ID NO: 20, or a combination thereof.

The present invention also features a host cell expression system expressing a C4.4a antibody according to the present invention. The present invention also features a labeled tissue sample (a labeled FFPE tissue sample), wherein the tissue sample is labeled with a C4.4a antibody according to the present invention.

The present invention also features a kit comprising a C4.4a antibody according to the present invention. The C4.4a antibody may be adapted for immunohistochemistry. In some embodiments, the kit further comprises a detection system (e.g., a chromogenic system, a fluorescence system, any other appropriate system) for making the C4.4a antibody visible. The kit may further comprise any other appropriate reagents, e.g., a secondary antibody directed to the C4.4a antibody, buffers, etc.

The present invention also features a method (e.g., automated method, manual method) of detecting C4.4a. In some embodiments, the method comprises providing a sample, contacting the sample with a C4.4a antibody according to the present invention, and making the antibody visible (e.g., via a detection system such as a chromogenic system, a fluorescence system, any other appropriate system). Detecting the antibody may be indicative of the presence of C4.4a.

The present invention also features methods of producing a C4.4a antibody (e.g., a C4.4a antibody according to the present invention). In some embodiments, the method comprises immunizing a host animal with the antibody using an immunogen as described herein.

The present invention also features a method of diagnosing a C4.4a-associated tumor (e.g., lung tumor, cervical tumor, skin carcinoma, esophageal tumor, and tumors with squamous differentiation), said method comprising detecting C4.4a according to a method of the present invention. Detection of C4.4a may be indicative of the C4.4a-associated tumor.

The present invention also features a labeled tissue sample (e.g., FFPE sample) labeled with a C4.4a antibody according to the present invention. The tissue sample may be obtained by a method according to the present invention.

The present invention also features a closed system for detecting C4.4a, e.g., a closed automated system adapted to perform a method according to the present invention, e.g., an automated immunohistochemistry assay.

The present invention also features a stainer machine programmed to perform a method according to the present invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SEQUENCE LISTING INCORPORATION BY REFERENCE

This application hereby incorporates-by-reference a sequence listing submitted herewith in a computer-readable format, having a file name of 32826_Sequence_ listing_ST25, created on Oct. 11, 2017, which is 61,904 bytes in size.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

TERMS

Figure 1A:
FIG. 1A shows the results of C4.4a immunohistochemistry on mouse xenograft tissues (SCC-T9, H293-T3, and MCF-7 models) using clone S42H9L5. DISCOVERY XT platform protocol: STD CC1, anti-human C4.4a antibody (at 1:400) for 16 min at room temperature (RT), standard ChromoMap DAB detection. Expression of C4.4A in mouse xenograft: SCC-T9—strong (+++); H293-T3—moderate (++); MCF-7—weak (+); PC3—negative (−). When clone S42H9L5 is used for IHC test, the staining intensity of mouse xenografts (SCC-T9, H293-T3, MCF-7, and PC3) matches the expression level of C4.4A.

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B."

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999, the disclosures of which are incorporated in their entirety herein by reference.

All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

In order to facilitate review of the various embodiments of the disclosure, the following explanations of specific terms are provided:

Antibody: A polypeptide that includes at least a light chain or heavy chain immunoglobulin variable region and specifically binds an epitope of an antigen (such as HER2 protein or ER protein). Antibodies include monoclonal antibodies, polyclonal antibodies, or fragments of antibodies. An antibody can be conjugated or otherwise labeled with a detectable label, such as an enzyme, hapten, or fluorophore.

Buffers: Buffer solutions are commonly used to maintain correct pH levels for biological and chemical systems. Many of the exemplary embodiments disclosed herein include using a buffer solution. Representative buffering agents or salts that may be present in the buffer include, but are not limited to Tris, Tricine, HEPES, MOPS, TAPS, Bicine, TAPSO, TES, PIPES, Cacodylate, SSC, MES, KCl, NaCl, potassium acetate, NH4-acetate, potassium glutamate, NH4Cl, ammonium sulphate, MgCl2, magnesium acetate and the like. One commonly used buffer solution is phosphate buffered saline (PBS). Another commonly used buffer solution is biotin ligase reaction buffer (0.1M KCl, 5.5 mM MgCl2, 50 mM Tris.HCl (pH=8.0), 0.05% Brij-35, 0.1 mM dithiothreitol (DTT), 3 mM ATP, and 60 µM biotin). The amount of buffering agent may range from about 5 to 150 mM, e.g., from about 10 to 100 mM, e.g., from about 20 to 50 mM, etc., however the buffering agent is not limited to those ranges. In some embodiments, the buffering agent helps provide a pH ranging from about 5.0 to about 9.5, e.g., 6.0 to 8.0, e.g., 6.5 to 7.5, etc. (e.g., at room temperature). Other agents that may be present in the buffer medium include chelating agents, such as EDTA, EGTA and the like.

Contacting: placement that allows association between two or more moieties, particularly direct physical association, for example both in solid form and/or in liquid form (for example, the placement of a biological sample, such as a biological sample affixed to a slide, in contact with a composition, such as a solution containing the probes disclosed herein).

Detectable label: A molecule or material that can produce a signal (such as a visual, electrical, or other signal) that indicates the presence and/or amount of a target (such as a protein or nucleic acid) in a sample. When conjugated to a specific binding molecule (for example, an antibody or nucleic acid probe), the detectable label can be used to locate and/or quantify the target to which the specific binding molecule is directed. A detectable label can be detected directly or indirectly, and several different detectable labels can be used in combination to detect one or more targets. For example, a first detectable label, such as a hapten conjugated to an antibody specific to a target, can be detected indirectly by using a second detectable label that is conjugated to a molecule that specifically binds the first detectable label. In addition, multiple detectable labels that can be separately detected can be conjugated to different specific binding molecules that specifically bind different targets to provide a multiplex assay that can provide detection of the multiple targets in a single sample.

Detectable labels include chromogenic, fluorescent, phosphorescent and/or luminescent molecules, catalysts (such as enzymes) that convert one substance into another substance to provide a detectable signal (such as by converting a colorless substance into a colored substance or vice versa, or by producing a precipitate or increasing sample turbidity), haptens that can be detected through antibody-hapten binding interactions using additional detectably labeled antibody conjugates, and paramagnetic and magnetic molecules or materials. Particular examples of detectable labels include: enzymes, such as horseradish peroxidase, alkaline phosphatase, acid phosphatase, glucose oxidase, β-galactosidase or β-glucuronidase; fluorophores, such as fluoresceins, luminophores, coumarins, BODIPY dyes, resorufins, and rhodamines (many additional examples of fluorescent molecules can be found in The Handbook—A Guide to Fluorescent Probes and Labeling Technologies, Molecular Probes, Eugene, Oreg.); nanoparticles, such as quantum dots (U.S. Pat. Nos. 6,815,064, 6,682,596 and 6,649,138, the disclosures of which are incorporated in their entirety herein by reference); metal chelates, such as DOTA and DPTA chelates of radioactive or paramagnetic metal ions like $Gd^{3+}$; and liposomes, for example, liposomes containing trapped fluorescent molecules. Where the detectable label includes an enzyme, a detectable substrate such as a chromogen, a fluorogenic compound, or a luminogenic compound is used in combination with the enzyme to generate a detectable signal (a wide variety of such compounds are commercially available, for example, from Life Technologies, Carlsbad, Calif.).

Alternatively, an enzyme can be used in a metallographic detection scheme. In some examples, metallographic detection methods include using an enzyme, such as alkaline phosphatase, in combination with a water-soluble metal ion and a redox-inactive substrate of the enzyme. The substrate is converted to a redox-active agent by the enzyme, and the redox-active agent reduces the metal ion, causing it to form a detectable precipitate (see, for example, U.S. Pat. Nos. 7,642,064; 7,632,652; the disclosures of which are incorporated in their entirety herein by reference). In other examples, metallographic detection methods include using an oxido-reductase enzyme (such as horseradish peroxidase) along with a water soluble metal ion, an oxidizing agent and a reducing agent, again to form a detectable precipitate (see, for example, U.S. Pat. No. 6,670,113, the disclosures of which are incorporated in their entirety herein by reference). Haptens are small molecules that can be bound by antibodies. Exemplary haptens include dinitrophenyl (DNP), biotin, digoxigenin (DIG), and fluorescein. Additional haptens include oxazole, pyrazole, thiazole, nitroaryl, benzofuran, triperpene, urea, thiourea, rotenoid, coumarin and cyclolignan haptens, such as those disclosed in U.S. Pat. No. 7,695,929, the disclosures of which are incorporated in their entirety herein by reference.

Hapten: A hapten is a molecule, typically a small molecule that can combine specifically with an antibody, but typically is substantially incapable of being immunogenic except in combination with a carrier molecule. Many haptens are known and frequently used for analytical procedures, such as di-nitrophenyl, biotin, digoxigenin, fluorescein, rhodamine, or combinations thereof. Plural different haptens may be coupled to a polymeric carrier. Moreover, compounds, such as haptens, can be coupled to another molecule using a linker, such as an NHS-PEG linker.

Immune complex: The binding of antibody to a soluble antigen forms an immune complex. The formation of an immune complex can be detected through conventional methods known to the person of ordinary skill in the art, for instance immunohistochemistry, immunoprecipitation, flow cytometry, immunofluorescence microscopy, ELISA, immunoblotting (e.g., Western blot), magnetic resonance imaging, CT scans, X-ray and affinity chromatography. Immunological binding properties of selected antibodies may be quantified using methods well known in the art.

Immunohistochemistry (IHC): A method of determining the presence or distribution of an antigen in a sample by detecting interaction of the antigen with a specific binding agent, such as an antibody. A sample is contacted with an antibody under conditions permitting antibody-antigen binding. Antibody-antigen binding can be detected by means of a detectable label conjugated to the antibody (direct detection) or by means of a detectable label conjugated to a secondary antibody, which binds specifically to the primary antibody (e.g., indirect detection).

Multiplex, -ed, -ing: Embodiments of the present invention allow multiple targets in a sample to be detected substantially simultaneously, or sequentially, as desired, using plural different conjugates. Multiplexing can include identifying and/or quantifying nucleic acids generally, DNA, RNA, peptides, proteins, both individually and in any and all combinations. Multiplexing also can include detecting two or more of a gene, a messenger and a protein in a cell in its anatomic context.

Probe: An isolated nucleic acid (such as an isolated synthetic oligonucleotide), attached to a detectable label or reporter molecule. Typical labels include radioactive isotopes, enzyme substrates, co-factors, ligands, chemiluminescent or fluorescent agents, haptens (including, but not limited to, DNP), and enzymes. Methods for labeling and guidance in the choice of labels appropriate for various purposes are discussed, e.g., in Sambrook et al. (In Molecular Cloning: A Laboratory Manual, CSHL, New York, 1989) and Ausubel et al. (In Current Protocols in Molecular Biology, Greene Publ. Assoc. and Wiley-Intersciences, 1992, the disclosures of which are incorporated in their entirety herein by reference).

Probes can be selected to provide a desired specificity, and may comprise at least 15, 20, 25, 30, 35, 40, 45, 50 or more nucleotides of a target nucleic acid. In particular examples, probes can include at least 100, 250, 500, 600, 1000, or more nucleotides of a target nucleic acid. In some examples, the probe includes segments of nucleotides that are from non-contiguous portions of a target nucleic acid, such as a HER2 genomic nucleic acid.

Sample: The term "sample" refers to any liquid, semi-solid or solid substance (or material) in or on which a target can be present. In particular, a sample can be a biological sample or a sample obtained from a biological material. Exemplary biological samples include tissue samples and/or cytology samples, for example, obtained from an animal subject, such as a human subject. In other examples, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A biological sample can also be a sample obtained from any organ or tissue (including a biopsy or autopsy specimen, such as a tumor biopsy) or can include a cell (whether a primary cell or cultured cell) or medium conditioned by any cell, tissue or organ.

Specific binding: A term that refers to the binding of agent that preferentially binds to a defined target (such as an antibody to a specific protein or antigen or a nucleic acid probe to a specific nucleic acid sequence). With respect to a target protein, "specifically binds" refers to the preferential association of an antibody or other ligand, in whole or part, with a specific polypeptide. "Specifically binds" refers to the preferential association of a nucleic acid probe, in whole or part, with a specific nucleic acid, when referring to a target nucleic acid.

A specific binding agent binds substantially only to a particular target. A minor amount of non-specific interaction may occur between a specific binding agent and a non-target protein or nucleic acid. Antibody to antigen specific binding typically results in greater than 2-fold, such as greater than 5-fold, greater than 10-fold, or greater than 100-fold increase in amount of bound antibody or other ligand (per unit time) to a target protein, as compared to a non-target protein. Immunoassay formats can be used to select antibodies that specifically react with a particular protein (such as antibodies that specifically bind HER2 protein or ER protein). See Harlow & Lane, *Antibodies, A Laboratory Manual*, Cold Spring Harbor Publications, New York (1988), for a description of immunoassay formats and conditions.

Specific binding of a nucleic acid probe to a target nucleic acid molecule typically results in greater than 2-fold, such as greater than 5-fold, greater than 10-fold, or greater than 100-fold increase in amount of bound nucleic acid probe to a target nucleic acid as compared to a non-target nucleic acid. A variety of ISH conditions are appropriate for selecting nucleic acid probes that bind specifically with a particular nucleic acid sequence (such as a HER2-specific probe or a chromosome 17 centromere probe).

Subject: Any multi-cellular vertebrate organism, such as human or non-human mammals (e.g., veterinary subjects).

DETAILED DESCRIPTION OF THE INVENTION

Figure 1A:
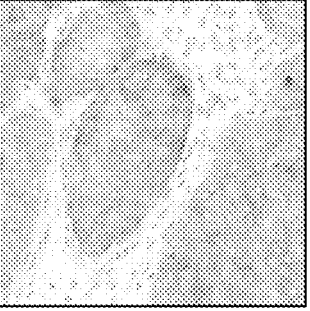
Figure 1A:
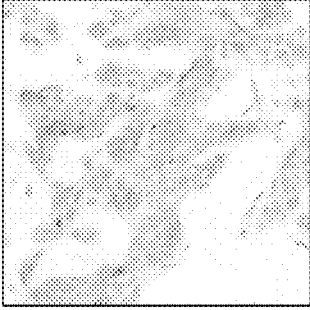
Figure 1A:
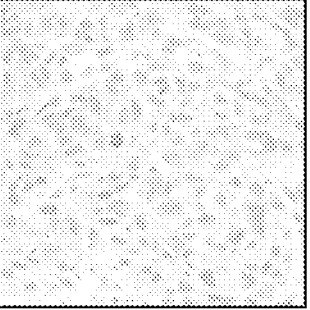
Figure 1B:
FIG. 1B shows the results of C4.4a immunohistochemistry on mouse xenograft tissues (SCC-T9, H293-T3, and MCF-7 models) like in FIG. 1A but with clone S20H1L1. Clone S20H1L1 showed weaker binding to C4.4a than clone S42H9L5 (the staining intensity is weaker in mouse xenografts).
Figure 1B:
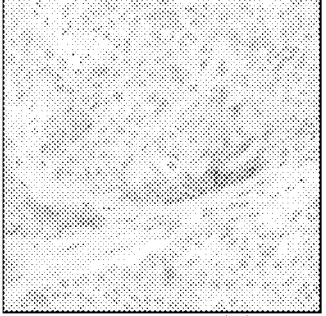
Figure 1B:
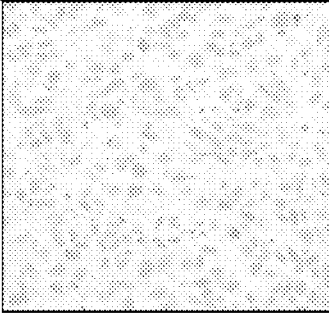
Figure 1B:
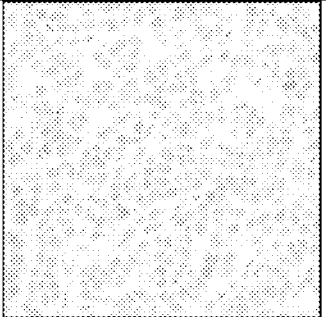
Figure 2A:
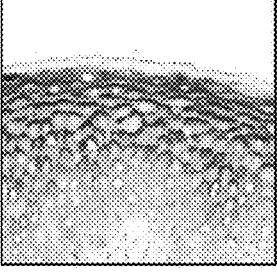
FIG. 2A shows the results of C4.4a immunohistochemistry on various human tissues (squamous cell carcinoma, skin, cervix, and esophagus) using clone S42H9L5. BenchMark XT platform protocol: STD CC1, anti-human C4.4a antibody (at 1:400) at RT, ultraView Dab Detection. Strong membrane staining is noticed in human skin squamous cell carcinoma, skin, cervix, and esophagus when clone S42H9L5 is used.
Figure 2A:
Figure 2A:
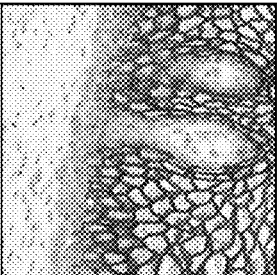
Figure 2A:
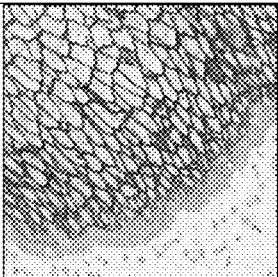
Figure 2B:
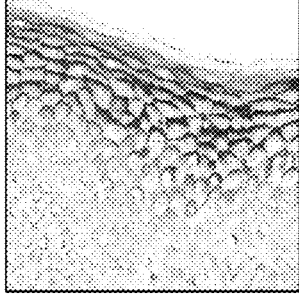
FIG. 2B shows the results of C4.4a immunohistochemistry on various human tissues (squamous cell carcinoma, skin, cervix, and esophagus) as in FIG. 2A but using clone S20H1L1. Strong membrane staining is noticed in human skin squamous cell carcinoma, skin, cervix, and esophagus when clone S20H1L1 is used.
Figure 2B:
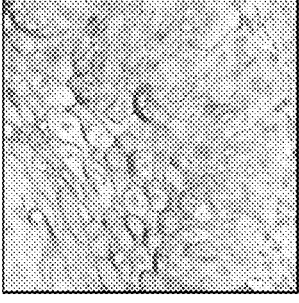
Figure 2B:
Figure 2B:
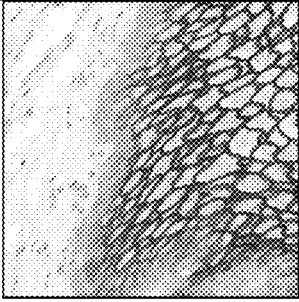

Referring now to FIG. 1-2, the present invention features antibodies directed to C4.4a, methods (e.g., immunohistochemistry) of detecting C4.4a using the antibodies disclosed herein, as well as methods for detecting C4.4a-associated cancers using the C4.4a antibodies disclosed herein. The present invention also includes any cDNA sequence encoding any peptide disclosed herein.

For reference, the sequence of C4.4a is shown below (antigen UniProt number O95274) (SEQ ID NO: 1):

```
             10         20         30         40         50
     MDPARKAGAQ AMIWTAGWLL LLLLRGGAQA LECYSCVQKA DDGCSPNKMK 60         70         80         90        100
     TVKCAPGVDV CTEAVGAVET IHGQFSLAVR GCGSGLPGKN DRGLDLHGLL 110        120        130        140        150
     AFIQLQQCAQ DRCNAKLNLT SRALDPAGNE SAYPPNGVEC YSCVGLSREA 160        170        180        190        200
     CQGTSPPVVS CYNASDHVYK GCFDGNVTLT AANVTVSLPV RGCVQDEFCT 210        220        230        240        250
     RDGVTGPGFT LSGSCCQGSR CNSDLRNKTY FSPRIPPLVR LPPPEPTTVA 260        270        280        290        300
     STTSVTTSTS APVRPTSTTK PMPAPTSQTP RQGVEHEASR DEEPRLTGGA 310        320        330        340
     AGHQDRSNSG QYRAKGGPQQ PHNKGCVAPT AGLAALLLAV AAGVLL
```

Immunogens

New Zealand White rabbits were immunized with recombinant protein (see epitope sequences and descriptions below) emulsified with complete Freund's adjuvant followed by a series of booster doses of immunogen emulsified with incomplete Freund's adjuvant.

| Sequence | | Description |
|---|---|---|
| S42H9L5 | Amino acids 31-308 as immunogen (SEQ ID NO: 2, see below) | Domain after signal peptide (Signal peptide is amino acids 1-30) was used as immunogen. ELISA testing using recombinant proteins for uPAR-Like domain 1 (amino acids 31-116) (SEQ ID NO: 3, see below) and uPAR-like domain 2 (amino acids 139-224) (SEQ ID NO: 4, see below) showed this clone binds to uPAR-like domain 2 (SEQ ID NO: 4, see below). |

-continued

| Sequence | Description |
| --- | --- |
| S20H1L1 | Amino acids 31-308 as immunogen (SEQ ID NO: 2) | Domain after signal peptide (amino acids 1-30). ELISA testing using recombinant proteins for uPAR-Like domain 1 (amino acids 31-116) (SEQ ID NO: 3, see below) and uPAR-like domain 2 (amino acids 139-224) (SEQ ID NO: 4, see below) showed this clone binds to uPAR-like domain 1 (SEQ ID NO: 3, see below). |

The immunogen used as described above corresponds to amino acids 31-308 of C4.4a:

(SEQ ID NO: 2)
LECYSCVQKADDGCSPNKMKTVKCAPGVDVCTEAVGAVETIHGQFSLAVR

GCGSGLPGKNDRGLDLHGLLAFIQLQQCAQDRCNAKLNLTSRALDPAGNE

SAYPPNGVECYSCVGLSREACQGTSPPVVSCYNASDHVYKGCFDGNVTLT

AANVTVSLPVRGCVQDEFCTRDGVTGPGFTLSGSCCQGSRCNSDLRNKTY

FSPRIPPLVRLPPPEPTTVASTTSVTTSTSAPVRPTSTTKPMPAPTSQTP

RQGVEHEASRDEEPRLTGGAAGHQDRSN.

For reference, the uPAR-like domain 1 corresponds to amino acids 31-116:

(SEQ ID NO: 3)
LECYSCVQKADDGCSPNKMKTVKCAPGVDVCTEAVGAVETIHGQFSLAVR

GCGSGLPGKNDRGLDLHGLLAFIQLQQCAQDRCNAK.

For reference, the uPAR-like domain 2 corresponds to amino acids 139-224:

(SEQ ID NO: 4)
ECYSCVGLSREACQGTSPPVVSCYNASDHVYKGCFDGNVTLTAANVTVSL

PVRGCVQDEFCTRDGVTGPGFTLSGSCCQGSRCNSD.

The present invention is not limited to the immunogen sequences disclosed herein. For example, in some embodiments, the immunogen comprises a fragment of SEQ ID NO: 2, e.g., all or a portion of the uPAR-like domain 1 (SEQ ID NO: 3), all or a portion of the uPAR-like domain 2 (SEQ ID NO: 4), etc. Fragments may be any appropriate length, e.g., between 270-277 amino acids, between 260-277 amino acids, between 250-277 amino acids, between 240-277 amino acids, between 230-277 amino acids, between 220-277 amino acids, between 210-277 amino acids, between 200-277 amino acids, between 190-277 amino acids, between 180-277 amino acids, between 170-277 amino acids, between 160-277 amino acids, between 150-277 amino acids, between 140-277 amino acids, between 130-277 amino acids, between 120-277 amino acids, between 110-277 amino acids, between 100-277 amino acids, between 90-277 amino acids, between 80-277 amino acids, between 70-277 amino acids, between 60-277 amino acids, between 50-277 amino acids, between 40-277 amino acids, etc. In some embodiments, the immunogen comprises a sequence that is at least 60% identical (e.g., at least 65% identical, at least 70% identical, at least 75% identical, at least 80% identical, at least 85% identical, at least 90% identical, at least 95% identical, at least 98% identical, at least 99% identical, etc.) to SEQ ID NO: 2. Shown below are non-limiting examples of other immunogen peptides, e.g., fragments of SEQ ID NO: 2:

| SEQ ID NO: | Amino Acid Length | Immunogen Sequence |
| --- | --- | --- |
| 5 | 260 | LECYSCVQKADDGCSPNKMKTVKCAPGVDVCTEAVGAVETIH GQFSLAVRGCGSGLPGKNDRGLDLHGLLAFIQLQQCAQDRC NAKLNLTSRALDPAGNESAYPPNGVECYSCVGLSREACQGTS PPVVSCYNASDHVYKGCFDGNVTLTAANVTVSLPVRGCVQDE FCTRDGVTGPGFTLSGSCCQGSRCNSDLRNKTYFSPRIPPLV RLPPPEPTTVASTTSVTTSTSAPVRPTSTTKPMPAPTSQTPRQ GVEHEASR |
| 6 | 250 | CVQKADDGCSPNKMKTVKCAPGVDVCTEAVGAVETIHGQFSL AVRGCGSGLPGKNDRGLDLHGLLAFIQLQQCAQDRCNAKLNL TSRALDPAGNESAYPPNGVECYSCVGLSREACQGTSPPVVS CYNASDHVYKGCFDGNVTLTAANVTVSLPVRGCVQDEFCTR DGVTGPGFTLSGSCCQGSRCNSDLRNKTYFSPRIPPLVRLPP PEPTTVASTTSVTTSTSAPVRPTSTTKPMPAPTSQTPRQGVE |
| 7 | 245 | LECYSCVQKADDGCSPNKMKTVKCAPGVDVCTEAVGAVETIH GQFSLAVRGCGSGLPGKNDRGLDLHGLLAFIQLQQCAQDRC NAKLNLTSRALDPAGNESAYPPNGVECYSCVGLSREACQGTS PPVVSCYNASDHVYKGCFDGNVTLTAANVTVSLPVRGCVQDE FCTRDGVTGPGFTLSGSCCQGSRCNSDLRNKTYFSPRIPPLV RLPPPEPTTVASTTSVTTSTSAPVRPTSTTKPMPAP |
| 8 | 200 | LECYSCVQKADDGCSPNKMKTVKCAPGVDVCTEAVGAVETIH GQFSLAVRGCGSGLPGKNDRGLDLHGLLAFIQLQQCAQDRC NAKLNLTSRALDPAGNESAYPPNGVECYSCVGLSREACQGTS |

-continued

| SEQ ID NO: | Amino Acid Length | Immunogen Sequence |
|---|---|---|
| | | PPVVSCYNASDHVYKGCFDGNVTLTAANVTVSLPVRGCVQDE FCTRDGVTGPGFTLSGSCCQGSRCNSDLRNKTY |
| 9 | 190 | CVQKADDGCSPNKMKTVKCAPGVDVCTEAVGAVETIHGQFSL AVRGCGSGLPGKNDRGLDLHGLLAFIQLQQCAQDRCNAKLNL TSRALDPAGNESAYPPNGVECYSCVGLSREACQGTSPPVVS CYNASDHVYKGCFDGNVTLTAANVTVSLPVRGCVQDEFCTR DGVTGPGFTLSGSCCQGSRCNSDL |
| 10 | 180 | TVKCAPGVDVCTEAVGAVETIHGQFSLAVRGCGSGLPGKNDR GLDLHGLLAFIQLQQCAQDRCNAKLNLTSRALDPAGNESAYP PNGVECYSCVGLSREACQGTSPPVVSCYNASDHVYKGCFDG NVTLTAANVTVSLPVRGCVQDEFCTRDGVTGPGFTLSGSCCQ GSRCNSDLRNKTY |
| 11 | 165 | TVKCAPGVDVCTEAVGAVETIHGQFSLAVRGCGSGLPGKNDR GLDLHGLLAFIQLQQCAQDRCNAKLNLTSRALDPAGNESAYP PNGVECYSCVGLSREACQGTSPPVVSCYNASDHVYKGCFDG NVTLTAANVTVSLPVRGCVQDEFCTRDGVTGPGFTLSGSC |
| 12 | 140 | LECYSCVQKADDGCSPNKMKTVKCAPGVDVCTEAVGAVETIH GQFSLAVRGCGSGLPGKNDRGLDLHGLLAFIQLQQCAQDRC NAKLNLTSRALDPAGNESAYPPNGVECYSCVGLSREACQGTS PPVVSCYNASDHVYK |
| 13 | 125 | PNKMKTVKCAPGVDVCTEAVGAVETIHGQFSLAVRGCGSGLP GKNDRGLDLHGLLAFIQLQQCAQDRCNAKLNLTSRALDPAGN ESAYPPNGVECYSCVGLSREACQGTSPPVVSCYNASDHVYK |
| 14 | 120 | LECYSCVQKADDGCSPNKMKTVKCAPGVDVCTEAVGAVETIH GQFSLAVRGCGSGLPGKNDRGLDLHGLLAFIQLQQCAQDRC NAKLNLTSRALDPAGNESAYPPNGVECYSCVGLSREA |
| 15 | 110 | CTEAVGAVETIHGQFSLAVRGCGSGLPGKNDRGLDLHGLLAFI QLQQCAQDRCNAKLNLTSRALDPAGNESAYPPNGVECYSCV GLSREACQGTSPPVVSCYNASDHVYK |
| 16 | 100 | CVQKADDGCSPNKMKTVKCAPGVDVCTEAVGAVETIHGQFSL AVRGCGSGLPGKNDRGLDLHGLLAFIQLQQCAQDRCNAKLNL TSRALDPAGNESAYPP |

The present invention is not limited to immunogens comprising SEQ ID NO: 2, fragments thereof, or sequences that have at least 60% identity with SEQ ID NO: 2. For example, in some embodiments, the immunogen comprises a fragment of full length C4.4a (SEQ ID NO: 1), e.g., amino acids 1-330, amino acids 1-310, amino acids 1-308, amino acids 1-300, amino acids 1-280, amino acids 1-250, amino acids 10-330, amino acids 10-310, amino acids 10-308, amino acids 10-300, amino acids 10-280, amino acids 10-250, amino acids 20-330, amino acids 20-310, amino acids 20-308, amino acids 20-300, amino acids 20-280, amino acids 20-250, amino acids 30-330, amino acids 30-310, amino acids 30-308, amino acids 30-300, amino acids 30-280, amino acids 30-250, etc. Fragments of SEQ ID NO: 1 may be any appropriate length, e.g., between 330-345 amino acids, between 300-345 amino acids, between 280-345 amino acids, between 250-345 amino acids, between 200-345 amino acids, between 150-345 amino acids, between 100-345 amino acids, between 50-345 amino acids, between 30-345 amino acids, etc. In some embodiments, the immunogen comprises a sequence that is at least 60% identical, 65% identical, 70% identical, 75% identical, 80% identical, 85% identical, 90% identical, 95% identical, 98% identical, 99% identical, etc., to SEQ ID NO: 1.

The C4.4a antibodies of the present invention may be derived according to methods described herein (e.g., see above), however the C4.4a antibody is not limited to such methods and may be made by any other appropriate means.

C4.4a Antibody Sequences and Configurations

As previously discussed, the present invention features antibodies directed to C4.4a, e.g., monoclonal C4.4a antibodies. Shown below are non-limiting examples variable region sequences of two C4.4 antibody clones: S42H9L5 and S20H1L1 (hereinafter also referred to as "S42" and "S20," respectively). In some embodiments, a C4.4a antibody of the present invention comprises one or more of the below sequences (SEQ ID NO: 17, SEQ ID NO: 18, SEQ ID NO: 19, SEQ ID NO: 20).

| Clone | Chain | Sequence |
|---|---|---|
| S42H9L5 | Heavy (SEQ ID NO: 17) | METGLRWLLLVAVLKGVQCQSLEESGGRLVKPDETLTL TCTVSGFSLNTVAISWVRQAPGKGLEWIGFIHPTVNTYY ARWAKGRFTISRASSTTVDLKVTSLTFEDAATYFCVRGN AHYDIWGPGTLVTVSLGQPKAPSVFPLAPCCGDTPSST VTLGCLVKGYLPEPVTVTWNSGTLTNGVRTFPS |

| Clone | Chain | Sequence |
|---|---|---|
| | Light (SEQ ID NO: 18) | MDTRAPTQLLGLLLLWLPGARCAFELTQTPSLVSAAVGG TVTISCQSSQSVYSDNYLAWYQQKPGQRPKLLIYKASDL ASGVPSRFKGSGSGTEFTLTISDLECADAATYYCQSYYG VSSDSNAFGGGTEVVVKGDPVAPTVLIFPPSADLVATGT VTIVCVANKYFPDVTVTWEV |
| S20H1L1 | Heavy (SEQ ID NO: 19) | METGLRWLLLVAVLKGVQCQEQLEESGGGLVKPGGTLT LTCTASGFSLISTYYICWVRQAPGKGLEWIGCIPLSHSVS WYANWVNGRFSISKTSSTTVTLKMASLTDADTATYFCG RGSSGWGVDSKLWGPGTLVTVSSGQPKAPSVFPLAPC CGDTPSSTVTLGCLVKGYLPEPVTVTWNSGTLTNGVRT FPS |
| | Light (SEQ ID NO: 20) | MDTRAPTQLLGLLLLWLPGAPFAAVLTQTPSPVSASVGG TVTINCQSSPSVASGYLSWFQQKPGQPPKLLIYRASTLV SGVPSRFKGSGSGTHFTLTISDVQCDDAATYYCAGAYS SRSDTTFGGGTEVVVKGDPVAPTVLIFPPAADQVATGTV TIVCVANKYFPDVTVTWEV |

For reference, the CDR and FR regions of the variable heavy and light chain sequences are highlighted below:

Clone S42 Heavy Chain

| Chain | Sequence |
|---|---|
| Signal peptide (SEQ ID NO: 21) | METGLRWLLLVAVLKGVQC |
| FR1 (SEQ ID NO: 22) | QSLEESGGRLVKPDETLTLTCTVSGFSLN |
| CDR1 (SEQ ID NO: 23) | TVAIS |
| FR2 (SEQ ID NO: 24) | WVRQAPGKGLEWIG |
| CDR2 (SEQ ID NO: 25) | FIHPTVNTYYARWAKG |
| FR3 (SEQ ID NO: 26) | RFTISRASSTTVDLKVTSLTFEDAATYFCVR |
| CDR3 (SEQ ID NO: 27) | GNAHYDI |
| FR4 (SEQ ID NO: 28) | WGPGTLVTVSL |

Clone S42 Light Chain

| Chain | Sequence |
|---|---|
| Signal peptide (SEQ ID NO: 29) | MDTRAPTQLLGLLLLWLPGARC |
| FR1 (SEQ ID NO: 30) | AFELTQTPSLVSAAVGGTVTISC |
| CDR1 (SEQ ID NO: 31) | QSSQSVYSDNYLA |
| FR2 (SEQ ID NO: 32) | WYQQKPGQRPKLLIY |
| CDR2 (SEQ ID NO: 33) | KASDLAS |
| FR3 (SEQ ID NO: 34) | GVPSRFKGSGSGTEFTLTISDLECADAATYYC |
| CDR3 (SEQ ID NO: 35) | QSYYGVSSDSNA |
| FR4 (SEQ ID NO: 36) | FGGGTEVVVK |

Clone S20 Heavy Chain

| Chain | Sequence |
|---|---|
| Signal peptide (SEQ ID NO: 37) | METGLRWLLLVAVLKGVQC |
| FR1 (SEQ ID NO: 38) | QEQLEESGGGLVKPGGTLTLTCTASGFSLI |
| CDR1 (SEQ ID NO: 39) | STYYIC |
| FR2 (SEQ ID NO: 40) | WVRQAPGKGLEWIG |
| CDR2 (SEQ ID NO: 41) | CIPLSHSVSWYANWVNG |
| FR3 (SEQ ID NO: 42) | RFSISKTSSTTVTLKMASLTDADTATYFCGR |
| CDR3 (SEQ ID NO: 43) | GSSGWGVDSKL |
| FR4 (SEQ ID NO: 44) | WGPGTLVTVSS |

Clone S20 Light Chain

| Chain | Sequence |
|---|---|
| Signal peptide (SEQ ID NO: 45) | MDTRAPTQLLGLLLLWLPGAPFA |
| FR1 (SEQ ID NO: 46) | AVLTQTPSPVSASVGGTVTINC |
| CDR1 (SEQ ID NO: 47) | QSSPSVASGYLS |

-continued

| Chain | Sequence |
|---|---|
| FR2 (SEQ ID NO: 48) | WFQQKPGQPPKLLIY |
| CDR2 (SEQ ID NO: 49) | RASTLVS |
| FR3 (SEQ ID NO: 50) | GVPSRFKGSGSGTHFTLTISDVQCDDAATYYC |
| CDR3 (SEQ ID NO: 51) | AGAYSSRSDTT |
| FR4 (SEQ ID NO: 52) | FGGGTEVVVK |

The antibodies of the present invention are not limited to comprising the sequences listed above (e.g., SEQ ID NO: 17, SEQ ID NO: 18, SEQ ID NO: 19, SEQ ID NO: 20). For example, in some embodiments, the C4.4a antibody comprises SEQ ID NO: 17, SEQ ID NO: 18, SEQ ID NO: 19, SEQ ID NO: 20, a fragment thereof, or a peptide that is at least 60% identical (e.g., at least 65% identical, at least 70% identical, at least 75% identical, at least 80% identical, at least 85% identical, at least 90% identical, at least 95% identical, at least 98% identical, at least 99% identical, etc.) to SEQ ID NO: 17, SEQ ID NO: 18, SEQ ID NO: 19, or SEQ ID NO: 20. In some embodiments, the fragment is between 20-60 amino acids, between 40-80 amino acids, between 60-100 amino acids, between 80-120 amino acids, between 100-140 amino acids, between 120-160 amino acids, between 140-180 amino acids, between 160-186 amino acids, between 160-190 amino acids, between 170-193 amino acids, etc. In some embodiments, the C4.4a antibody comprises a peptide that is at least 60% identical (e.g., at least 65% identical, at least 70% identical, at least 75% identical, at least 80% identical, at least 85% identical, at least 90% identical, at least 95% identical, at least 98% identical, at least 99% identical, etc.) to a fragment (e.g., between 20-60 amino acids, between 40-80 amino acids, between 60-100 amino acids, between 80-120 amino acids, between 100-140 amino acids, between 120-160 amino acids, between 140-180 amino acids, between 160-186 amino acids, between 160-190 amino acids, between 170-193 amino acids, etc.) of one of SEQ ID NO: 17, SEQ ID NO: 18, SEQ ID NO: 19, or SEQ ID NO: 20.

In some embodiments, the C4.4a antibody may comprise a recombinant protein comprising two or more (e.g., three, four, five, six, seven, eight, nine, 10, 11, 12, etc.) peptides derived from any of: SEQ ID NO: 17, SEQ ID NO: 18, SEQ ID NO: 19, SEQ ID NO: 20, a fragment (between 20-60 amino acids, between 40-80 amino acids, between 60-100 amino acids, between 80-120 amino acids, between 100-140 amino acids, between 120-160 amino acids, between 140-180 amino acids, between 160-186 amino acids, between 160-190 amino acids, between 170-193 amino acids, etc.) thereof, a peptide that is at least 60% identical (e.g., at least 65% identical, at least 70% identical, at least 75% identical, at least 80% identical, at least 85% identical, at least 90% identical, at least 95% identical, at least 98% identical, at least 99% identical, etc.) to SEQ ID NO: 17, SEQ ID NO: 18, SEQ ID NO: 19, or SEQ ID NO: 20, and/or a peptide that is at least 60% identical (e.g., at least 65% identical, at least 70% identical, at least 75% identical, at least 80% identical, at least 85% identical, at least 90% identical, at least 95% identical, at least 98% identical, at least 99% identical, etc.) to a fragment (e.g., between 20-60 amino acids, between 40-80 amino acids, between 60-100 amino acids, between 80-120 amino acids, between 100-140 amino acids, between 120-160 amino acids, between 140-180 amino acids, between 160-186 amino acids, between 160-190 amino acids, between 170-193 amino acids, etc.) of one of SEQ ID NO: 17, SEQ ID NO: 18, SEQ ID NO: 19, or SEQ ID NO: 20. For example, the C4.4a antibody may comprise a first peptide section and a second peptide section, each selected from the above list (SEQ ID NO: 17, SEQ ID NO: 18, SEQ ID NO: 19, SEQ ID NO: 20, a fragment (between 20-60 amino acids, between 40-80 amino acids, between 60-100 amino acids, between 80-120 amino acids, between 100-140 amino acids, between 120-160 amino acids, between 140-180 amino acids, between 160-186 amino acids, between 160-190 amino acids, between 170-193 amino acids, etc.) thereof, a peptide that is at least 60% identical (e.g., at least 65% identical, at least 70% identical, at least 75% identical, at least 80% identical, at least 85% identical, at least 90% identical, at least 95% identical, at least 98% identical, at least 99% identical, etc.) to SEQ ID NO: 17, SEQ ID NO: 18, SEQ ID NO: 19, or SEQ ID NO: 20, and/or a peptide that is at least 60% identical (e.g., at least 65% identical, at least 70% identical, at least 75% identical, at least 80% identical, at least 85% identical, at least 90% identical, at least 95% identical, at least 98% identical, at least 99% identical, etc.) to a fragment (e.g., between 20-60 amino acids, between 40-80 amino acids, between 60-100 amino acids, between 80-120 amino acids, between 100-140 amino acids, between 120-160 amino acids, between 140-180 amino acids, between 160-186 amino acids, between 160-190 amino acids, between 170-193 amino acids, etc.) of one of SEQ ID NO: 17, SEQ ID NO: 18, SEQ ID NO: 19, or SEQ ID NO: 20.). In some embodiments, the first peptide section and second peptide section are contiguous. In some embodiments, the first peptide section and the second peptide section are separated by one or more additional amino acids (e.g., a linker). As an example, a C4.4a antibody may comprise a first peptide section corresponding to amino acids 1-110 of SEQ ID NO: 17 and another peptide section corresponding to amino acids 20-140 of SEQ ID NO: 18, possibly separated by a linker (e.g., a linker, e.g., a linker having 1 amino acid, 2 amino acids, 3 amino acids, 4 amino acids, 5 amino acids, 6 amino acids, 8-10 amino acids, 10-20 amino acids, more than 20 amino acids, etc.). And, in some embodiments, said first peptide section may be downstream of said second peptide section.

Below are shown non-limiting examples of sequences that are at least 60% identical to SEQ ID NO: 17, SEQ ID NO: 18, SEQ ID NO: 19, or SEQ ID NO: 20. The present invention is in no way limited to these sequences or the particular amino acids that vary in the below sequences as compared to the original sequence. Note: "X" refers to any appropriate amino acid substitution.

| SEQ ID NO: | Description | Sequence (note: X refers to any appropriate amino acid substitution) |
|---|---|---|
| 61 | Sequence at least 90% identical to SEQ ID NO: 17 | MXTGLRWLLLVXVLKGVQCQSLEXSGGRLXXPDETL XLTCTVSGFSLNTVAISXVRQXPGKGLEWIGFIHPTVN TYYARWXKGRFTISRASSTTVXLKVTSLTFEDAATYFC VRGNXHYDIWXPGTLVTVSXGQPKAPSVFPLXPCCX DTPSSTVTLXCLVKXYLPEPVTVTWNSXTLTNGVRTF PS |
| 62 | Sequence at least 80% identical to SEQ ID NO: 18 | MXTRAPTQXLGLLXLWXPXARCXFELTQTPSLVSXAV GXTVTISCQSXQSVYSXNYLAXYQQKPXQRPKXLIYK XSXLXSXXPSRFKXSGSXTXFTLTISDLECADAXTYXC QSYYGVSXDSNAFXGGTEVXVKGDPVXPTVLIFPXSX XLVXTGTVXIVCVXNKYFPDVTVXWXV |
| 63 | Sequence at least 95% identical to SEQ ID NO: 19 | METGLRWLLLVXVLKGVQCQEXLEXSGGGLVKPGGT LTLTCTASXFSLISTYYICWVRQAPGKGLEWIGCIPLSH SVSWYXNWVNGRFSISKTSSTXVTLKMASLTDADTAT YFCXRGSSGWGVDSKLWGPGTLVTVXSGQPKAPSV FPLXPCCGDTPSSTVTLGCLVKGYLPEPVTVTWNSGT LTNGVRTFPS |
| 64 | Sequence at least 70% identical to SEQ ID NO: 20 | MXTRAXTQLLGLXXXWLPXAPXAAXLTQTXSPVXAXV XXTVXINXQSSPXVASGYLSXFXQKPXQPPXLLIYRXX TLXSGXPSRFKGXXSGTHFTLTISDVQXXXXATYYXXX XYSSRXDXTXGXXTEVXXKGDPXXPTXLIFPPAXDQV ATGXVTIXCVAXKYFPXVTXTWXX |

As previously discussed, the present invention includes any cDNA that encodes any peptide disclosed herein, e.g., a cDNA that encodes any of the aforementioned antibody sequences (or any antibody sequence according to the present invention).

Epitope Regions

The C4.4a antibody binds specifically to a particular sequence or region of C4.4a, e.g., a C4.4a epitope. Non-limiting examples of sequences or regions containing an epitope to which the antibody may bind include the uPAR-like domain 1 (e.g., SEQ ID NO: 3, SEQ ID NO: 53), the uPAR-like domain 2 (e.g., SEQ ID NO: 4, SEQ ID NO: 57), fragments thereof (e.g., between 5-10 amino acids, between 10-20 amino acids, between 10-30 amino acids, between 10-40 amino acids, between 20-40 amino acids, between 20-50 amino acids, between 30-50 amino acids, between 30-60 amino acids, between 30-70 amino acids, between 40-70 amino acids, between 40-80 amino acids, between 50-80 amino acids, between 50-90 amino acids, between 60-90 amino acids, between 50-100 amino acids, between 60-100 amino acids, etc.), peptides that are at least 60% identical (e.g., at least 65% identical, at least 70% identical, at least 75% identical, at least 80% identical, at least 85% identical, at least 90% identical, at least 95% identical, at least 98% identical, at least 99% identical, etc.) to the uPAR-like domain 1 (e.g., SEQ ID NO: 3, SEQ ID NO: 53) or the uPAR-like domain 2 (e.g., SEQ ID NO: 4, SEQ ID NO: 57), peptides that are at least 60% identical to fragments of the uPAR-like domain 1 or the uPAR-like domain 2, etc. The uPAR-like domain 1 is not limited to amino acids 31-116 of C4.4a. For example, in some embodiments, the uPAR-like domain 1 comprises amino acids 33-126 of C4.4a (SEQ ID NO: 53), amino acids 32-116, amino acids 31-126, amino acids 31-125, amino acids 31-124, amino acids 31-123, amino acids 31-122, amino acids 31-121, amino acids 31-120, amino acids 31-119, amino acids 31-118, amino acids 31-118, amino acids 31-117, amino acids 31-115, amino acids 31-114, amino acids 31-113, amino acids 31-112, amino acids 31-111, amino acids 31-110, amino acids 32-110, amino acids 32-112, amino acids 32-114, amino acids 32-118, amino acids 32-119, amino acids 32-120, amino acids 33-128, amino acids 31-127, amino acids 34-119, amino acids 36-122, etc. The uPAR-like domain 2 is not limited to amino acids 139-224 of C4.4a. For example, in some embodiments, the uPAR-like domain 2 comprises amino acids 140-222 of C4.4a (SEQ ID NO: 53), amino acids 139-215, amino acids 139-216, amino acids 139-217, amino acids 139-218, amino acids 139-219, amino acids 139-220, amino acids 139-222, amino acids 139-223, amino acids 139-225, amino acids 139-226, amino acids 139-227, amino acids 138-215, amino acids 138-216, amino acids 138-217, amino acids 138-218, amino acids 138-219, amino acids 138-220, amino acids 138-222, amino acids 138-223, amino acids 138-225, amino acids 138-226, amino acids 138-227, amino acids 140-215, amino acids 140-216, amino acids 140-217, amino acids 140-218, amino acids 140-219, amino acids 140-220, amino acids 140-223, amino acids 140-224, amino acids 140-225, amino acids 140-226, amino acids 140-227, etc.

Further, the epitope is not limited to regions within the uPAR-like domains. In some embodiments, amino acids around the uPAR-like domains may also be part of the epitope.

Non-limiting examples of regions containing epitopes to which the C4.4a antibodies may bind are shown below:

| SEQ ID NO: | Amino Acid Length | Epitope Sequence |
|---|---|---|
| 3 | 86 | LECYSCVQKADDGCSPNKMKTVKCAPGVDVCTEAVGAVE TIHGQFSLAVRGCGSGLPGKNDRGLDLHGLLAFIQLQQCA QDRCNAK (amino acids 31-116 of C4.4a) |

-continued

| SEQ ID NO: | Amino Acid Length | Epitope Sequence |
|---|---|---|
| 53 | 94 | CYSCVQKADDGCSPNKMKTVKCAPGVDVCTEAVGAVETI HGQFSLAVRGCGSGLPGKNDRGLDLHGLLAFIQLQQCAQ DRCNAKLNLTSRALDP (amino acids 33-126 of C4.4a) |
| 54 | 55 | PNKMKTVKCAPGVDVCTEAVGAVETIHGQFSLAVRGCGS GLPGKNDRGLDLHGLL (amino acids 46-100 of C4.4a) |
| 55 | 47 | KTVKCAPGVDVCTEAVGAVETIHGQFSLAVRGCGSGLPGK NDRGLDL (amino acids 50-96 of C4.4a) |
| 56 | 97 | YSCVQKADDGCSPNKMKTVKCAPGVDVCTEAVGAVETIH GQFSLAVRGCGSGLPGKNDRGLDLHGLLAFIQLQQCAQD RCNAKLNLTSRALDPAGNE (amino acids 34-130 of C4.4a) |
| 4 | 86 | ECYSCVGLSREACQGTSPPVVSCYNASDHVYKGCFDGNV TLTAANVTVSLPVRGCVQDEFCTRDGVTGPGFTLSGSCCQ GSRCNSD (amino acids 139-224 of C4.4a) |
| 57 | 83 | CYSCVGLSREACQGTSPPVVSCYNASDHVYKGCFDGNVT LTAANVTVSLPVRGCVQDEFCTRDGVTGPGFTLSGSCCQ GSRCN (amino acids 140-222 of C4.4a) |
| 58 | 84 | ECYSCVGLSREACQGTSPPVVSCYNASDHVYKGCFDGNV TLTAANVTVSLPVRGCVQDEFCTRDGVTGPGFTLSGSCCQ GSRCN (amino acids 139-222 of C4.4a) |
| 59 | 71 | CYSCVGLSREACQGTSPPVVSCYNASDHVYKGCFDGNVT LTAANVTVSLPVRGCVQDEFCTRDGVTGPGFT (amino acids 140-210 of C4.4a) |
| 60 | 73 | LSREACQGTSPPVVSCYNASDHVYKGCFDGNVTLTAANVT VSLPVRGCVQDEFCTRDGVTGPGFTLSGSCCQG (amino acids 146-218 of C4.4a) |

In some embodiments, the region containing the epitope comprises SEQ ID NO: 3, SEQ ID NO: 4, SEQ ID NO 53, SEQ ID NO 54, SEQ ID NO 55, SEQ ID NO 56, SEQ ID NO 57, SEQ ID NO 58, SEQ ID NO 59, SEQ ID NO 60, a fragment (e.g., between 5-10 amino acids, between 10-20 amino acids, between 10-30 amino acids, between 10-40 amino acids, between 20-40 amino acids, between 20-50 amino acids, between 30-50 amino acids, between 30-60 amino acids, between 30-70 amino acids, between 40-70 amino acids, between 40-80 amino acids, between 50-80 amino acids, between 50-85 amino acids, between 60-85 amino acids, etc.) thereof, a peptide that is at least 60% identical (e.g., at least 65% identical, at least 70% identical, at least 75% identical, at least 80% identical, at least 85% identical, at least 90% identical, at least 95% identical, at least 98% identical, at least 99% identical, etc.) to SEQ ID NO: 3, SEQ ID NO: 4, SEQ ID NO 53, SEQ ID NO 54, SEQ ID NO 55, SEQ ID NO 56, SEQ ID NO 57, SEQ ID NO 58, SEQ ID NO 59, or SEQ ID NO 60, a peptide that is at least 60% identical (e.g., at least 65% identical, at least 70% identical, at least 75% identical, at least 80% identical, at least 85% identical, at least 90% identical, at least 95% identical, at least 98% identical, at least 99% identical, etc.) to a fragment (e.g., between 5-10 amino acids, between 10-20 amino acids, between 10-30 amino acids, between 10-40 amino acids, between 20-40 amino acids, between 20-50 amino acids, between 30-50 amino acids, between 30-60 amino acids, between 30-70 amino acids, between 40-70 amino acids, between 40-80 amino acids, between 50-80 amino acids, between 50-85 amino acids, between 60-85 amino acids, etc.) of SEQ ID NO: 3, SEQ ID NO: 4, SEQ ID NO 53, SEQ ID NO 54, SEQ ID NO 55, SEQ ID NO 56, SEQ ID NO 57, SEQ ID NO 58, SEQ ID NO 59, or SEQ ID NO 60, or a combination thereof.

In some embodiments, the antibody binds to and/or the epitope comprises a C4.4a glycosylation site, e.g., amino acid 118, 163, 176, 183, or 326.

The present invention is not limited to clone S42 and clone S20. The present invention also features a C4.4a antibody (e.g., a monoclonal antibody) or C4.4a binding fragment, wherein the C4.4a antibody or binding fragment has the same epitopic specificity as an antibody selected from the group consisting of clone S42H9L5 and clone S20H1L1. For example, the C4.4a antibody may have a different sequence than S42 and/or S20, but the C4.4a antibody may have the same or similar specificity for the epitope(s) of S42 and/or S20.

As previously discussed, C4.4a antibodies disclosed herein may be produced by immunizing a host with a C4.4a protein (e.g., an immunogen as previously discussed) or related peptide. The host may include but is not limited to a mouse, a rat, a rabbit, In some embodiments, the host model is a mouse model, a rat model, a rabbit (e.g., New Zealand white rabbit), donkey, sheep; however the host is not limited to these examples. In some embodiments, recombinant C4.4a antibodies may be produced using a host cell expression system. Examples of host cell expression systems include but are not limited to HEK293 cells or derivatives thereof, mammalian cells (e.g., CHO, HELA, SP20, etc.), insect cells, yeast (e.g., *P. pastoris*), plant cells (e.g., tobacco), prokaryotic systems (e.g., *E. coli*), etc. The present invention is not limited to the expression systems disclosed herein.

The present invention also features a labeled tissue sample (e.g., a formalin-fixed paraffin-embedded sample), wherein the tissue sample is labeled with a C4.4a antibody according to the present invention. The tissue sample may be obtained by a method according to the present invention.

The present invention also features a kit comprising a C4.4a antibody according to the present invention, e.g., a kit for immunohistochemistry, e.g., for use on a formalin-fixed paraffin-embedded sample, wherein the C4.4a antibody is adapted for immunohistochemistry. Kits for IHC are well known to one of ordinary skill in the art. In some embodiments, the kit comprises a detection system (e.g., a chromogenic system, a fluorescence system, any other appropriate system) for making the C4.4a antibody visible. In some embodiments, the kit comprises any other appropriate reagents, e.g., a secondary antibody directed to the C4.4a antibody, buffers, etc.

In some embodiments, the antibody is adapted for use in immunohistochemistry (IHC) assays. In some embodiments, the antibody is adapted for use assays other than IHC assays, e.g., for western blotting or other antibody-related applications.

As previously discussed, the present invention also features methods of detecting C4.4a using the antibodies disclosed herein, as well as methods for detecting C4.4a-associated cancers using the C4.4a antibodies disclosed herein.

The present invention also features a method (e.g., automated method, manual method) of detecting C4.4a. In some embodiments, the method comprises providing a sample, contacting the sample with a C4.4a antibody according to the present invention, and making the antibody visible (e.g., via a detection system such as a chromogenic system, a fluorescence system, any other appropriate system). Detecting the antibody may be indicative of the presence of C4.4a.

The present invention also features a method of diagnosing a C4.4a-associated tumor (e.g., lung tumor, cervical tumor, skin carcinoma, esophageal tumor). The method may comprise detecting C4.4a according to a method of the present invention. Detection of C4.4a may be indicative of the C4.4a-associated tumor.

The present invention also features a stainer machine programmed to perform a method according to the present invention. For example, the stainer machine comprises components for performing an automated immunohistochemistry method. The stainer machine may comprise a program that allows for the methods of the present invention to be performed. The present invention also features a closed system for detecting C4.4a, e.g., a closed automated system adapted to perform a method according to the present invention.

Computers typically include known components, such as a processor, an operating system, system memory, memory storage devices, input-output controllers, input-output devices, and display devices. It will also be understood by those of ordinary skill in the relevant art that there are many possible configurations and components of a computer and may also include cache memory, a data backup unit, and many other devices. Examples of input devices include a keyboard, a cursor control devices (e.g., a mouse), a microphone, a scanner, and so forth. Examples of output devices include a display device (e.g., a monitor or projector), speakers, a printer, a network card, and so forth. Display devices may include display devices that provide visual information, this information typically may be logically and/or physically organized as an array of pixels. An interface controller may also be included that may comprise any of a variety of known or future software programs for providing input and output interfaces. For example, interfaces may include what are generally referred to as "Graphical User Interfaces" (often referred to as GUI's) that provide one or more graphical representations to a user. Interfaces are typically enabled to accept user inputs using means of selection or input known to those of ordinary skill in the related art. The interface may also be a touch screen device. In the same or alternative embodiments, applications on a computer may employ an interface that includes what are referred to as "command line interfaces" (often referred to as CLI's). CLI's typically provide a text based interaction between an application and a user. Typically, command line interfaces present output and receive input as lines of text through display devices. For example, some implementations may include what are referred to as a "shell" such as Unix Shells known to those of ordinary skill in the related art, or Microsoft Windows Powershell that employs object-oriented type programming architectures such as the Microsoft .NET framework.

Those of ordinary skill in the related art will appreciate that interfaces may include one or more GUI's, CLI's or a combination thereof. A processor may include a commercially available processor such as a Celeron, Core, or Pentium processor made by Intel Corporation, a SPARC processor made by Sun Microsystems, an Athlon, Sempron, Phenom, or Opteron processor made by AMD Corporation, or it may be one of other processors that are or will become available. Some embodiments of a processor may include what is referred to as multi-core processor and/or be enabled to employ parallel processing technology in a single or multi-core configuration. For example, a multi-core architecture typically comprises two or more processor "execution cores". In the present example, each execution core may perform as an independent processor that enables parallel execution of multiple threads. In addition, those of ordinary skill in the related will appreciate that a processor may be configured in what is generally referred to as 32 or 64 bit architectures, or other architectural configurations now known or that may be developed in the future.

A processor typically executes an operating system, which may be, for example, a Windows type operating system from the Microsoft Corporation; the Mac OS X operating system from Apple Computer Corp.; a Unix or Linux-type operating system available from many vendors or what is referred to as an open source; another or a future operating system; or some combination thereof. An operating system interfaces with firmware and hardware in a well-known manner, and facilitates the processor in coordinating and executing the functions of various computer programs that may be written in a variety of programming languages. An operating system, typically in cooperation with a processor, coordinates and executes functions of the other components of a computer. An operating system also provides scheduling, input-output control, file and data management, memory management, and communication control and related services, all in accordance with known techniques.

System memory may include any of a variety of known or future memory storage devices that can be used to store the desired information and that can be accessed by a computer. Computer readable storage media may include volatile and non-volatile, removable and non-removable media implemented in any method or technology for storage of information such as computer readable instructions, data structures, program modules, or other data. Examples include any commonly available random access memory (RAM), read-only memory (ROM), electronically erasable programmable read-only memory (EEPROM), digital versatile disks (DVD), magnetic medium, such as a resident hard disk or tape, an optical medium such as a read and write compact disc, or other memory storage device. Memory storage devices may include any of a variety of known or future devices, including a compact disk drive, a tape drive, a removable hard disk drive, USB or flash drive, or a diskette drive. Such types of memory storage devices typically read from, and/or write to, a program storage medium such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with memory storage device. In some embodiments, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts. Input-output controllers could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers could include controllers for any of a variety of known display devices for presenting information to a user, whether a human or a machine, whether local or remote. In the presently described embodiment, the functional elements of a computer communicate with each other via a system bus. Some embodiments of a computer may communicate with some functional elements using network or other types of remote communications. As will be evident to those skilled in the relevant art, an instrument control and/or a data processing application, if implemented in software, may be loaded into and executed from system memory and/or a memory storage device. All or portions of the instrument control and/or data processing applications may also reside in a read-only memory or similar device of the memory storage device, such devices not requiring that the instrument control and/or data processing applications first be loaded through input-output controllers. It will be understood by those skilled in the relevant art that the instrument control and/or data processing applications, or portions of it, may be loaded by a processor, in a known manner into system memory, or cache memory, or both, as advantageous for execution. Also, a computer may include one or more library files, experiment data files, and an internet client stored in system memory. For example, experiment data could include data related to one or more experiments or assays, such as detected signal values, or other values associated with one or more sequencing by synthesis (SBS) experiments or processes. Additionally, an internet client may include an application enabled to access a remote service on another computer using a network and may for instance comprise what are generally referred to as "Web Browsers". In the present example, some commonly employed web browsers include Microsoft Internet Explorer available from Microsoft Corporation, Mozilla Firefox from the Mozilla Corporation, Safari from Apple Computer Corp., Google Chrome from the Google Corporation, or other type of web browser currently known in the art or to be developed in the future. Also, in the same or other embodiments an Internet client may include, or could be an element of, specialized software applications enabled to access remote information via a network such as a data processing application for biological applications.

A network may include one or more of the many various types of networks well known to those of ordinary skill in the art. For example, a network may include a local or wide area network that may employ what is commonly referred to as a TCP/IP protocol suite to communicate. A network may include a network comprising a worldwide system of interconnected computer networks that is commonly referred to as the Internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

EXAMPLES

The following examples describe non-limiting examples of experiments using methods, compositions, and systems of the present invention.

Example 1

IHC protocol on mouse xenografts: DISCOVERY XT protocol used on mouse xenograft tissues (SCC-T9—strong; H293-T3—moderate; MCF-7—weak; PC3—negative) using DISCOVERY XT platform. Briefly, selects Std CC1 cell conditioning for antigen retrieval, dilute anti-C4.4a antibody clone SP246 (a S42H9L5 clone) at 1:400 (3 µg/ml) in antibody diluent (Catalog Number 251-018, Ventana), incubates the primary antibody for 16 min at room temperature, selects standard ChromoMap DAB detection. Lastly, target antigen is detected using a chromogenic substrate (DAB), followed with hematoxylin counterstaining for 1 minute. See FIG. 1A, FIG. 1B.

Example 2

IHC protocol on human tissues: Standard ultraView Universal DAB Detection Kit protocol is used on human tissues (skin, skin squamous cell carcinoma, cervix, and esophagus) using BenchMark Ultra platform (Ventana Medical System). Briefly, selects StdCC1 cell conditioning for antigen retrieval, dilutes anti-C4.4a antibody clone SP245 (a S20H1L1 clone) at 1:400 (3 µg/ml) in antibody diluent (Catalog Number 251-018, Ventana), incubates the primary antibody for 16 min at room temperature, selects standard ultraView Universal DAB Detection protocol. Lastly, target antigen is detected using DAB, followed with hematoxylin counterstaining for 1 minute. See FIG. 2A, FIG. 2B.

As used herein, the term "about" refers to plus or minus 10% of the referenced number.

The abbreviation "aa" means "amino acid".

The disclosures of the following documents are incorporated in their entirety by reference herein: WO2014183119; US20120295803; US20130066055; WO2011158883; US20120321619; EP1220919.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

FURTHER DISCLOSED EMBODIMENTS

Embodiment 1

A monoclonal C4.4a antibody comprising SEQ ID NO: 17, SEQ ID NO: 18, SEQ ID NO: 19, SEQ ID NO: 20, or a combination thereof.

Embodiment 2

A monoclonal C4.4a antibody specific for an epitope within a uPAR-like domain 1 or a uPAR-like domain 2, said antibody comprising SEQ ID NO: 17, SEQ ID NO: 18, SEQ ID NO: 19, SEQ ID NO: 20, or a combination thereof.

Embodiment 3

A monoclonal C4.4a antibody comprising SEQ ID NO: 17, SEQ ID NO: 18, SEQ ID NO: 19, SEQ ID NO: 20, a fragment thereof, a peptide that is at least 60% identical to SEQ ID NO: 17, SEQ ID NO: 18, SEQ ID NO: 19, or SEQ ID NO: 20, a peptide that is at least 60% identical to a fragment of SEQ ID NO: 17, SEQ ID NO: 18, SEQ ID NO: 19, or SEQ ID NO: 20, or a combination thereof.

Embodiment 4

The antibody of embodiment 3, wherein the fragment is at least 20 amino acids in length.

Embodiment 5

The antibody of embodiment 3, wherein the fragment is at least 60 amino acids in length.

Embodiment 6

The antibody of embodiment 3, wherein the fragment is at least 100 amino acids in length.

Embodiment 7

The antibody of any of embodiments 1-3, wherein the antibody is raised by immunizing a host with a peptide comprising SEQ ID NO: 1, SEQ ID NO: 2, SEQ ID NO: 3, SEQ ID NO: 4, a fragment thereof, a peptide that is at least 60% identical to SEQ ID NO: 1, SEQ ID NO: 2, SEQ ID NO: 3, or SEQ ID NO: 4, a peptide that is at least 60% identical to a fragment of SEQ ID NO: 1, SEQ ID NO: 2, SEQ ID NO: 3, or SEQ ID NO: 4, or a combination thereof.

Embodiment 8

The antibody of embodiment 7, wherein the fragment is at least 20 amino acids in length.

Embodiment 9

The antibody of any of embodiments 1-3, wherein the antibody binds to an epitope within a region, said region comprising SEQ ID NO: 3, SEQ ID NO: 4, SEQ ID NO 53, SEQ ID NO 54, SEQ ID NO 55, SEQ ID NO 56, SEQ ID NO 57, SEQ ID NO 58, SEQ ID NO 59, SEQ ID NO 60, a fragment thereof, a peptide that is at least 60% identical to SEQ ID NO: 3, SEQ ID NO: 4, SEQ ID NO 53, SEQ ID NO 54, SEQ ID NO 55, SEQ ID NO 56, SEQ ID NO 57, SEQ ID NO 58, SEQ ID NO 59, or SEQ ID NO 60, a peptide that is at least 60% identical to a fragment of SEQ ID NO: 3, SEQ ID NO: 4, SEQ ID NO 53, SEQ ID NO 54, SEQ ID NO 55, SEQ ID NO 56, SEQ ID NO 57, SEQ ID NO 58, SEQ ID NO 59, or SEQ ID NO 60, or a combination thereof.

Embodiment 10

The antibody of embodiment 9, wherein the fragment is at least 20 amino acids in length.

Embodiment 11

A monoclonal anti-C4.4a antibody or monoclonal C4.4a binding fragment, said antibody or binding fragment has the same epitopic specificity as an antibody selected from the group consisting of clone S42H9L5 and clone S20H1L1.

Embodiment 12

A monoclonal C4.4a antibody, wherein the antibody binds specifically to a C4.4a epitope, the epitope is within a region, said region comprising SEQ ID NO: 3, SEQ ID NO: 4, SEQ ID NO 53, SEQ ID NO 54, SEQ ID NO 55, SEQ ID NO 56, SEQ ID NO 57, SEQ ID NO 58, SEQ ID NO 59, SEQ ID NO 60, a fragment thereof, a peptide that is at least 60% identical to SEQ ID NO: 3, SEQ ID NO: 4, SEQ ID NO 53, SEQ ID NO 54, SEQ ID NO 55, SEQ ID NO 56, SEQ ID NO 57, SEQ ID NO 58, SEQ ID NO 59, or SEQ ID NO 60, a peptide that is at least 60% identical to a fragment of SEQ ID NO: 3, SEQ ID NO: 4, SEQ ID NO 53, SEQ ID NO 54, SEQ ID NO 55, SEQ ID NO 56, SEQ ID NO 57, SEQ ID NO 58, SEQ ID NO 59, or SEQ ID NO 60, or a combination thereof.

Embodiment 13

The antibody of embodiment 12, wherein the fragment is at least 20 amino acids in length.

Embodiment 14

A monoclonal C4.4a antibody derived from immunizing a host with an immunogen comprising SEQ ID NO: 1, SEQ ID NO: 2, SEQ ID NO: 3, SEQ ID NO: 4, a fragment thereof, a peptide that is at least 60% identical to SEQ ID NO: 1, SEQ ID NO: 2, SEQ ID NO: 3, SEQ ID NO: 4, a peptide that is at least 60% identical to a fragment of SEQ ID NO: 1, SEQ ID NO: 2, SEQ ID NO: 3, or SEQ ID NO: 4, or a combination thereof.

Embodiment 15

The antibody of embodiment 14, wherein the fragment is at least 20 amino acids in length.

Embodiment 16

The antibody of embodiment 14, wherein the host is a rabbit host.

Embodiment 17

The antibody of any of embodiment 1-16, wherein the antibody is produced in a host expression system.

Embodiment 18

A cDNA encoding a C4.4a antibody according to any of embodiments 1-17.

Embodiment 19

A host cell expression system expressing an antibody according to any of embodiments 1-17.

Embodiment 20

The host cell expression system of embodiment 19, wherein the host cells are HEK293 cells.

Embodiment 21

A labeled tissue sample, wherein the tissue sample is labeled with a C4.4a antibody according to any of embodiments 1-17.

Embodiment 22

The tissue sample of embodiment 21, wherein the tissue sample is a formalin-fixed paraffin-embedded tissue sample.

Embodiment 23

A kit comprising a C4.4a antibody according to any of embodiments 1-17.

Embodiment 24

The kit of embodiment 23, wherein the antibody is adapted for immunohistochemistry.

Embodiment 25

The kit of embodiment 23 further comprising a detection system for making the C4.4a antibody visible.

Embodiment 26

The kit of embodiment 25, wherein the detection system comprises a chromogenic detection system.

Embodiment 27

The kit of embodiment 25, wherein the detection system comprises a fluorescence detection system.

Embodiment 28

A method of detecting C4.4a, said method comprising:
a. contacting a sample with a C4.4a antibody according to any of embodiments 1-17; and
b. making the antibody visible;
wherein detecting the C4.4a antibody is indicative of the presence of C4.4a.

Embodiment 29

The method of embodiment 28, wherein the method is automated.

Embodiment 30

The method of embodiment 28, wherein the method is manual.

Embodiment 31

The method of any of embodiments 28-30, wherein the step of making the antibody visible comprises contacting the antibody with a chromogenic detection system or a fluorescence detection system.

Embodiment 32

A method of producing a C4.4a antibody, said method comprising immunizing an animal with a peptide comprising SEQ ID NO: 1, SEQ ID NO: 2, SEQ ID NO: 3, SEQ ID NO: 4, a fragment thereof, a peptide that is at least 60% identical to SEQ ID NO: 1, SEQ ID NO: 2, SEQ ID NO: 3, or SEQ ID NO: 4, a peptide that is at least 60% identical to a fragment of SEQ ID NO: 1, SEQ ID NO: 2, SEQ ID NO: 3, or SEQ ID NO: 4, or a combination thereof.

Embodiment 33

The method of embodiment 32, wherein the fragment is at least 20 amino acids in length.

Embodiment 34

The method of embodiment 32, wherein the antibody is a C4.4a antibody according to any of embodiments 1-17.

Embodiment 35

A method of diagnosing a C4.4a-associated tumor, said method comprising detecting C4.4a according to any of embodiments 28-31, wherein detection of C4.4a is indicative of the C4.4a-associated tumor.

Embodiment 36

A labeled tissue sample labeled with a C4.4a antibody, the tissue sample is obtained by a method according to any of embodiments 28-31.

Embodiment 37

A closed system for detecting C4.4a, the system is automated and is adapted to perform a method according to any of embodiments 28-31.

Embodiment 38

A system comprising:
a. a stainer machine;
b. a processor; and
c. a memory coupled to the processor, the memory stores computer-readable instructions that, when executed by the processor, cause the processor to perform operations comprising:
  i. instructing the stainer machine to deposit a C4.4a antibody onto a sample; and
  ii. instructing the stainer machine to deposit a detection reagent onto the sample so as to make the C4.4a antibody visible.

Embodiment 39

The system of embodiment 38, wherein the stainer machine comprises at least a dispenser for dispensing the C4.4a antibody onto the sample.

Embodiment 40

The system of embodiment 38, wherein the operations further comprise instructing the stainer machine to incubate the sample at a temperature sufficient for binding of the C4.4a antibody to its target.

Embodiment 41

The system of embodiment 40, wherein the stainer machine comprises a heat pad for incubating the sample.

Embodiment 42

The system of embodiment 38, wherein the operations further comprise instructing the stainer machine to wash the sample with a wash buffer before the detection reagent is deposited onto the sample.

Embodiment 43

The system of embodiment 42, wherein the stainer machine comprises a dispenser for dispensing a wash buffer onto the sample.

Embodiment 44

The system of embodiment 38, wherein the operations further comprise instructing the stainer machine to incubate the sample in a cell conditioning buffer prior to the depositing of the C4.4a antibody.

Embodiment 45

The system of embodiment 44, wherein the operations further comprise instructing the stainer machine to deposit a deparaffinizing buffer onto the sample prior to the depositing of the cell conditioning buffer.

Embodiment 46

The system of embodiment 45, wherein the operations further comprise instructing the stainer to bake the sample prior to the depositing of the deparaffinizing buffer onto the sample.

Embodiment 47

The system of embodiment 38, wherein the detection reagent comprises a secondary antibody, a chromogenic detection reagent, or a combination thereof.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

The invention claimed is:

1. A monoclonal C4.4a antibody specific for an epitope within a uPAR-like domain 2 within a human C4.4a protein, said monoclonal C4.4a antibody comprising a heavy chain variable region comprising heavy chain complementarity determining regions H-CDR1, H-CDR2, and H-CDR3, wherein H-CDR1 comprises SEQ ID NO: 23, H-CDR2 comprises SEQ ID NO: 25, and H-CDR3 comprises SEQ ID NO: 27, and further comprising a light chain variable region comprising light chain complementarity determining regions L-CDR1, L-CDR2, and L-CDR3, wherein L-CDR1 comprises SEQ ID NO: 31, L-CDR2 comprises SEQ ID NO: 33, and L-CDR3 comprises SEQ ID NO: 35.

2. The monoclonal C4.4a antibody of claim 1, wherein the heavy chain variable region comprises SEQ ID NO: 17.

3. The monoclonal C4.4a antibody of claim 1, wherein the uPAR like domain 2 comprises SEQ ID NO: 4.

4. The monoclonal C4.4a antibody of claim 1, wherein the heavy chain variable region further comprises heavy chain framework regions H-FR1, H-FR2, H-FR3, and H-FR4, wherein H-FR1 comprises SEQ ID NO: 22, H-FR2 comprises SEQ ID NO: 24, H-FR3 comprises SEQ ID NO: 26, and H-FR4 comprises SEQ ID NO: 28.

5. The monoclonal C4.4a antibody of claim 1, wherein the light chain variable region further comprises light chain framework regions L-FR1, L-FR2, L-FR3, and L-FR4, wherein L-FR1 comprises SEQ ID NO: 30, L-FR2 comprises SEQ ID NO: 32, L-FR3 comprises SEQ ID NO: 34, and L-FR4 comprises SEQ ID NO: 36.

6. The monoclonal C4.4a antibody of claim 1, wherein the light chain variable region comprises SEQ ID NO: 18.

7. The monoclonal C4.4a antibody of claim 2, wherein the light chain variable region comprises SEQ ID NO: 18.

8. A kit comprising a C4.4a antibody according to claim 1.

9. The kit of claim 8, wherein the monoclonal C4.4a antibody is adapted for immunohistochemistry.

10. The kit of claim 8 further comprising a detection system for making the C4.4a antibody visible.

11. The kit of claim 10, wherein the detection system comprises a chromogenic detection system.

12. The kit of claim 10, wherein the detection system comprises a fluorescence detection system.

13. A method of labeling a biological sample for human C4.4a protein, said method comprising:
   a. contacting a sample with a C4.4a antibody according to claim 1; and
   b. making the antibody bound to the sample visible.

14. The method of claim 13, wherein the biological sample is a tissue sample.

15. The method of claim 14, wherein the tissue sample is a formalin fixed, paraffin embedded (FFPE) tissue sample.

16. The method of claim 13, wherein the step of making the antibody visible comprises contacting the antibody with a chromogenic detection system or a fluorescence detection system.

17. The method of claim 13, wherein the biological sample is from a human.

18. The method of claim 17, wherein the biological sample is a tissue sample.

19. The method of claim 18, wherein the tissue sample is a formalin fixed, paraffin embedded (FFPE) tissue sample of a human tumor.

20. A method of diagnosing a C4.4a-associated tumor, said method comprising obtaining a tumor sample, labeling the tumor sample for human C4.4a protein according to the method of claim 13, and detecting the presence or absence of visible antibody, wherein detection of visible C4.4a antibody is indicative that the tumor is the C4.4a-associated tumor.

* * * * *